(12) United States Patent
Cho et al.

(10) Patent No.: US 10,803,315 B2
(45) Date of Patent: Oct. 13, 2020

(54) ELECTRONIC DEVICE AND METHOD FOR PROCESSING INFORMATION ASSOCIATED WITH FOOD

(71) Applicant: Samsung Electronics Co., Ltd., Gyeonggi-do (KR)

(72) Inventors: Jungchan Cho, Gyeonggi-do (KR); Sanghyun Lee, Gyeonggi-do (KR); Jihwan Choe, Gyeonggi-do (KR); Ji-Yoon Park, Gyeonggi-do (KR); Byungjun Son, Gyeonggi-do (KR); Yang-Geun Oh, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 16/239,737

(22) Filed: Jan. 4, 2019

(65) Prior Publication Data

US 2019/0213416 A1    Jul. 11, 2019

(30) Foreign Application Priority Data

Jan. 8, 2018 (KR) .................. 10-2018-0002476

(51) Int. Cl.
*G06F 3/00* (2006.01)
*G06K 9/00* (2006.01)
(Continued)

(52) U.S. Cl.
CPC ..... *G06K 9/00671* (2013.01); *G06F 3/04817* (2013.01); *G06F 3/04845* (2013.01);
(Continued)

(58) Field of Classification Search
CPC ............... G06F 19/328; G06F 19/3418; G06F 19/3475; G06F 19/3481; G06F 3/0482;
(Continued)

(56) References Cited

U.S. PATENT DOCUMENTS 7,541,548 B1   6/2009  Sze et al.
8,690,578 B1   4/2014  Nusbaum et al.
(Continued)

FOREIGN PATENT DOCUMENTS

JP  2006-105655 A    4/2006
JP  2013037648 A  *  2/2013  ............. G06Q 50/22
(Continued)

OTHER PUBLICATIONS

International Search Report dated Apr. 8, 2019.
(Continued)

*Primary Examiner* — Di Xiao
(74) *Attorney, Agent, or Firm* — Cha & Reiter, LLC.

(57) ABSTRACT

An electronic device is disclosed herein, including a camera, display, processor and memory storing instructions, executable by the processor to: obtain and display an image using the camera, identify food items in the image, obtain nutritional information corresponding to each food item, obtain recommendation information including recommended consumption quantities associated with each food item, and display indications based on the recommended consumption quantities. In another embodiment, the processor is configured to: display indications indicating a recommended consumption quantity of each food item included in an image obtained through the at least one camera, detect a user input changing a recommended consumption quantity of a particular food item associated with a first indication to a new target consumption quantity, and change sizes of the first indication and a second indication different from the first indication, responsive to the user input.

20 Claims, 22 Drawing Sheets

(51) Int. Cl.
  *H04M 1/725* (2006.01)
  *G06F 3/0481* (2013.01)
  *G06F 3/0484* (2013.01)
  *G09B 19/00* (2006.01)
  *G16H 20/60* (2018.01)
  *G06F 3/0482* (2013.01)
  *G06T 7/50* (2017.01)
  *G06F 3/0488* (2013.01)

(52) U.S. Cl.
  CPC ......... *G09B 19/0092* (2013.01); *G16H 20/60* (2018.01); *H04M 1/72522* (2013.01); *G06F 3/0482* (2013.01); *G06F 3/04883* (2013.01); *G06K 2209/17* (2013.01); *G06T 7/50* (2017.01); *H04M 2250/52* (2013.01)

(58) Field of Classification Search
  CPC ............. G06F 3/0488; G06F 16/24575; G06F 16/583; G06F 16/9535; G06F 19/00; G06F 21/32; G06F 16/951; G06F 3/013; G06F 9/451; G06F 16/183; G06F 16/25; G06F 16/252; G06F 17/28
  See application file for complete search history.

(56) References Cited

U.S. PATENT DOCUMENTS

| | | |
|---|---|---|
| 9,442,100 B2 | 9/2016 | Connor |
| 2012/0096405 A1 | 4/2012 | Seo |
| 2013/0166334 A1* | 6/2013 | Liberty .................. G06Q 10/02 705/5 |
| 2013/0335418 A1* | 12/2013 | Kim ...................... G06Q 10/00 345/424 |
| 2015/0135132 A1* | 5/2015 | Josephson ............ G06F 3/0482 715/784 |
| 2016/0035248 A1* | 2/2016 | Gibbs .................. G06T 7/0002 434/127 |
| 2016/0321951 A1 | 11/2016 | Kim et al. |
| 2017/0046980 A1* | 2/2017 | Mehta ................ G09B 19/0092 |
| 2017/0316489 A1* | 11/2017 | Sampara ............. G06Q 10/087 |
| 2018/0149583 A1 | 5/2018 | Pi |
| 2018/0286276 A1 | 10/2018 | Lee et al. |

FOREIGN PATENT DOCUMENTS

| | | | | |
|---|---|---|---|---|
| JP | 2016-17932 A | | 2/2016 | |
| KR | 10-2006-0122111 A | | 11/2006 | |
| KR | 20120039102 A | * | 4/2012 | ......... G06F 3/04883 |
| KR | 10-2015-0124824 A | | 11/2015 | |
| KR | 20160128017 A | * | 11/2016 | ......... G09B 19/0092 |
| KR | 20170031517 A | * | 3/2017 | ............. G06Q 50/22 |
| KR | 10-1789732 B1 | | 10/2017 | |
| WO | 2015/170244 A1 | | 11/2015 | |

OTHER PUBLICATIONS

Korean Search Report dated May 13, 2019.
Korean Search Report dated Sep. 5, 2019.
Korean Search Report dated Mar. 24, 2020.
Korean Search Report dated May 4, 2020.
Korean Search Report dated Jul. 7, 2020.
Indian Search Report dated Aug. 21, 2020.

* cited by examiner

ELECTRONIC DEVICE AND METHOD FOR PROCESSING INFORMATION ASSOCIATED WITH FOOD

CROSS-REFERENCE TO RELATED APPLICATION(S)

This application is based on and claims priority under 35 U.S.C. § 119 to Korean Patent Application No. 10-2018-0002476, filed on Jan. 8, 2018, in the Korean Intellectual Property Office, the disclosure of which is incorporated by reference herein in its entirety.

BACKGROUND

1) Field

Various embodiments relate to an electronic device and a method for processing information associated with food.

2) Description of Related Art

The above information is presented as background information only to assist with an understanding of the present disclosure. No determination has been made, and no assertion is made, as to whether any of the above might be applicable as prior art with regard to the present disclosure.

With the development of technology, many electronic devices can now recognize objects captured within an image obtained by a camera. These electronic devices can provide information related to the recognized object.

SUMMARY

With a growing consciousness with regards to health, there is increasing interest in diet management. As electronic devices, such as a smartphone and a wearable device, are widely used, healthcare applications using an electronic device are being developed. Therefore, there may be desirable solutions for an electronic device to intuitively provide information on food intake.

The technical subjects pursued in the present disclosure may not be limited to the above mentioned technical subjects, and other technical subjects which are not mentioned may be clearly understood, through the following descriptions, by those skilled in the art of the present disclosure.

An electronic device according to various embodiments may include: at least one camera, at least one display, at least one processor, and a memory storing programming instructions executable by the at least one processor to cause the electronic device to obtain and display an image using the at least one camera, identify a plurality of food items in the image, obtain nutritional information corresponding to each of the plurality of food items, obtain recommendation information a recommended consumption quantities associated with each of the plurality of food items based on the nutritional information, display a plurality of indications based on the recommended consumption quantities in association with the plurality of food items.

An electronic device according to various embodiments may include: at least one camera, at least one display, at least one processor, and a memory storing programming instructions executable by the at least one processor to cause the electronic device to display indications indicating a recommended consumption quantity of each food item included in an image obtained through the at least one camera, detect a user input changing a recommended consumption quantity of a particular food item associated with a first indication to a new target consumption quantity, and change sizes of the first indication and a second indication different from the first indication, responsive to the user input.

A method for operating an electronic device according to various embodiments may include: obtaining an image using at least one camera of the electronic device; identifying a plurality of objects associated with a plurality of food from the image; obtaining nutritional information corresponding to each of the plurality of objects; obtaining information on a recommended intake associated with the plurality of food on the basis of the nutritional information; and displaying a plurality of indications for indicating the recommended intake in association with the plurality of objects included in the image.

A method for operating an electronic device according to various embodiments may include: displaying indications for indicating a recommended intake of each of food along with an image that is obtained through at least one camera of the electronic device and includes objects associated with the food; detecting a user input for changing a recommended intake of food associated with a first indication among the food to a target intake; and changing a size of the first indication among the indications and to change a size of a second indication, distinct from the first indication, among the indications on the basis of the user input.

A non-transitory computer-readable storage medium according to various embodiments may store one or more programs to implement: an operation of obtaining an image using at least one camera of an electronic device associated with the storage medium; an operation of identifying a plurality of objects associated with a plurality of food from the image; an operation of obtaining information on a recommended intake associated with the plurality of food on the basis of nutritional information; an operation of displaying the image; and an operation of displaying a plurality of indications for indicating the information on the recommended intake in association with the plurality of objects included in the image.

A non-transitory computer-readable storage medium according to various embodiments may store one or more programs to implement: an operation of displaying indications for indicating a recommended intake of each of food along with an image that is obtained through at least one camera of an electronic device associated with the storage medium and includes objects associated with the food; an operation of detecting a user input for changing a recommended intake of food associated with a first indication among the food to a target intake; and an operation of changing a size of the first indication among the indications and to change a size of a second indication, distinct from the first indication, among the indications on the basis of the user input.

An electronic device and a method thereof according to various embodiments may provide an image including an object associated with food through an intuitive user interface, thereby guiding a user on the intake of adequate food.

Effects which can be acquired by the present disclosure are not limited to the above described effects, and other effects that have not been mentioned may be clearly understood by those skilled in the art from the following description.

BRIEF DESCRIPTION OF THE DRAWINGS

The above and other aspects, features, and benefits of certain embodiments of the present disclosure will be more

DETAILED DESCRIPTION

Figure 1:
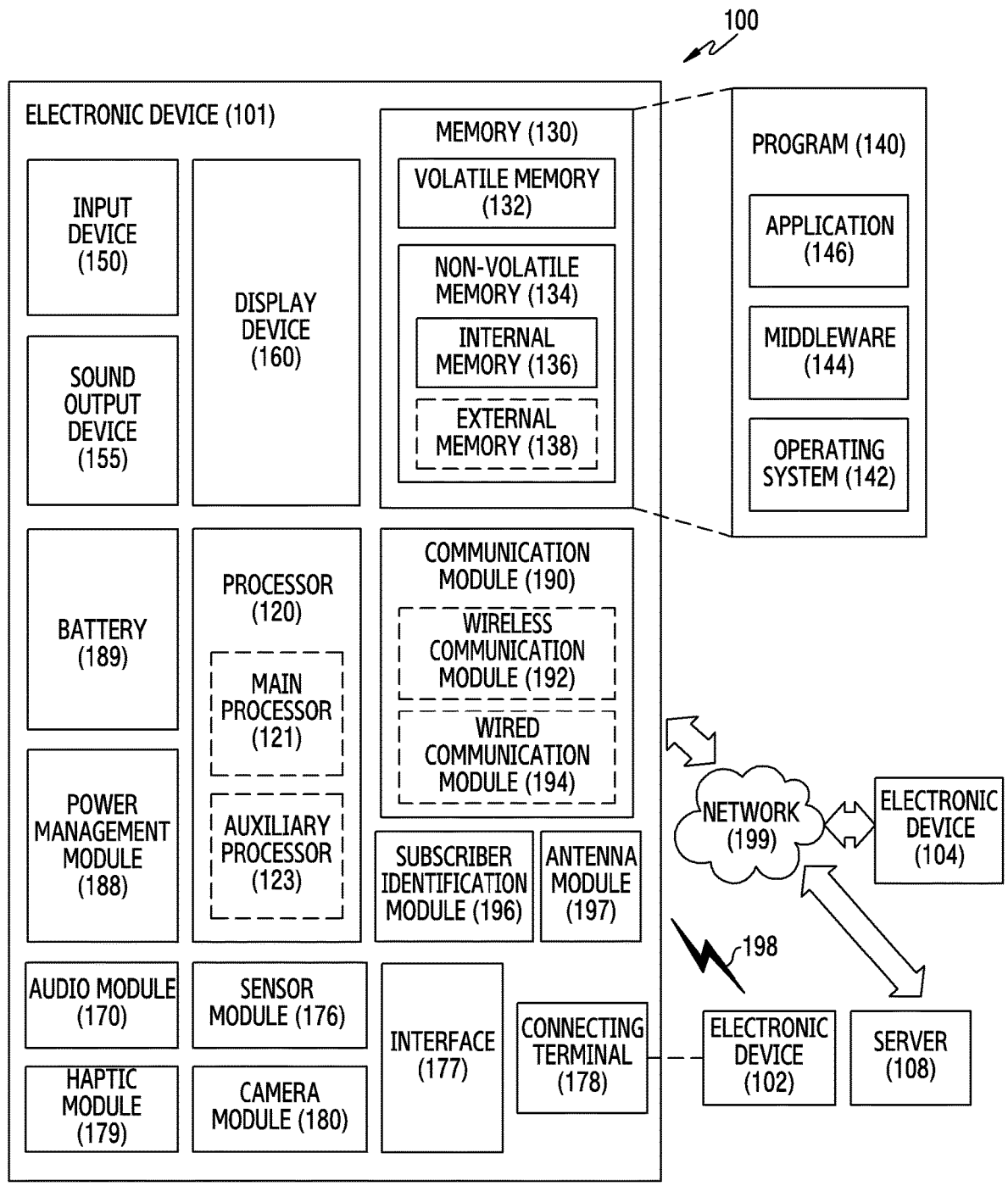
FIG. 1 is a block diagram illustrating an electronic device 101 in a network environment 100 according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN))). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element implemented using a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
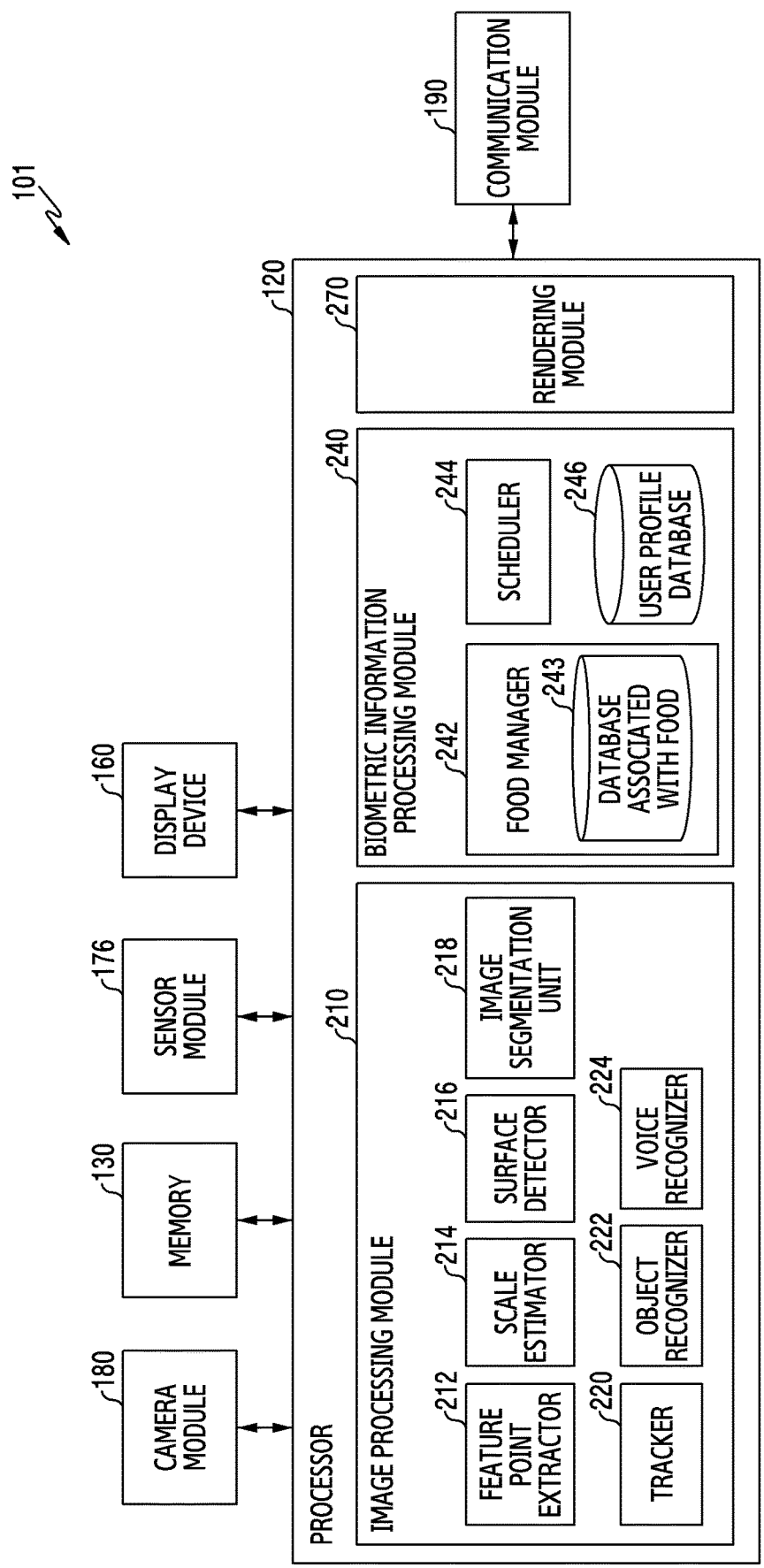
FIG. 2 illustrates an example of the functional configuration of an electronic device according to various embodiments.

FIG. 2 illustrates an example of the functional configuration of an electronic device according to various embodiments. This functional configuration may be included in the electronic device 101 shown in FIG. 1 or may be implemented in the electronic device 101.

Referring to FIG. 2, the electronic device 101 may include a processor 120, a memory 130, a display device 160, a sensor module 176, a camera module 180, and a communication module 190.

In various embodiments, the processor 120 may include the processor 120 shown in FIG. 1, the memory 130 may include the memory 130 shown in FIG. 1, the display device 160 may include the sensor module 176 shown in FIG. 1, the camera module 180 may include the camera module 180 shown in FIG. 1, and the communication module 190 may include at least one of the communication module 190 shown in FIG. 1 and the interface 177 shown in FIG. 1.

In various embodiments, the processor 120 may include an image processing module 210, a biometric information processing module 240, and a rendering module 270 and may execute instructions included in the memory 130 to drive the image processing module 210, the biometric information processing module 240, and the rendering module 270.

In various embodiments, the image processing module 210 may process an image obtained by the camera module 180 (e.g., at least one camera). The image may be associated with food. For example, the image may include a plurality of objects associated with a plurality of food. In various embodiments, the image processing module 210 may refer to an application for an artificial intelligence service (e.g., Bixby Vision™). In various embodiments, the image processing module 210 may include a feature point extractor 212, a scale estimator 214, a surface detector 216, an image segmentation unit 218, a tracker 220, an object recognizer 222, and a voice recognizer 224.

In various embodiments, the feature point extractor 212 may extract at least one feature from an image obtained by the camera module 180 to identify what is a main subject for photography in the image. In various embodiments, the feature point extractor 212 may extract at least one feature to identify a main object among a plurality of objects included in the image. In various embodiments, the feature point extractor 212 may extract at least one feature to identify what the image is about. For example, the processor 120 (or the image processing module 210) may extract at least one feature from the image using the feature point extractor 212, thereby identifying that the image is associated with food.

In various embodiments, the scale estimator 214 may estimate the amount (volume, mass, and the like) of food associated with an object included in an image obtained by the camera module 180 on the basis of depth information (and/or length information) associated with the image. In various embodiments, the depth information may refer to information obtained to change or convert the image, which is configured in two dimensions (2D), into a three-dimensional (3D) image. In various embodiments, the depth information may be obtained by emitting light, such as a laser and infrared rays, from the electronic device 101 while acquiring the image. For example, the depth information may be obtained on the basis of information on a wavelength based on the reflection of infrared rays emitted from the electronic device 101 while acquiring the image. In various embodiments, the depth information may be obtained by acquiring images through two or more cameras having different characteristics. In various embodiments, the depth information may be obtained through pre-processing or post-processing of an acquired image. For example, the depth information may be obtained by identifying the distance of each object included in the image from a reference point. In various embodiments, the depth information may be obtained using the parallax of left and right images using a stereo matching device that uses a camera for a left image and a camera for a right image. In various embodiments, the depth information may be obtained on the basis of the recognition of an audio signal (e.g., an audio signal associated with the type and amount of a menu) received while acquiring the image. For example, the depth information may be obtained from one image obtained by a camera using a trained model. In various embodiments, the scale estimator 214 may estimate the size of the object on the basis of the depth information, thereby estimating the amount of the food associated with the object.

In various embodiments, the surface detector 216 may obtain information on at least one of a surface, the curvature, and a texture of an object in an image obtained by the camera module 180 on the basis of the image. The surface detector 216 may obtain information for recognizing that the object is associated with food at least on the basis of the obtained information.

In various embodiments, the image segmentation unit 218 may divide an object included in an image obtained by the camera module 180 from the image. In various embodiments, the image segmentation unit 218 may identify or extract the object from the image at least on the basis of information on the continuity of the image, depth information associated with the image, information on colors in the image, information on a saliency map associated with the image (e.g., data on the unique quality of each pixel in the image), or indexing information associated with the image. The image segmentation unit 218 may divide the object from the image to recognize which food the object is associated with. In various embodiments, information on the divided object may be provided for recognition to a database stored in the memory 130. For example, the processor 120 may search or retrieve the database using the information on the object, thereby identifying which food the object is associated with. In various embodiments, the information on the divided object may be provided for recognition to an external electronic device (e.g., the server 108) related to the electronic device 101 via the communication module 190. For example, the external electronic device may retrieve a database included in the external electronic device using the received information on the object, thereby identifying which food the object is associated with.

In various embodiments, the tracker 220 may track a key object (e.g., an object associated with food) included in an image being acquired through the camera module 180 from the image. In various embodiments, the tracker 220 may track a predetermined marker included in the image being acquired through the camera module 180. In various embodiments, the processor 120 may monitor, using the tracker 220, whether the state of the image being acquired is changed or the intention of a user acquiring the image is changed.

In various embodiments, the object recognizer 222 may recognize which food an object divided by the image segmentation unit 218 is associated with. For example, the object recognizer 222 may recognize that the divided object is associated with a pork cutlet. For this recognition, the object recognizer 222 may interwork with the external electronic device or may be liked with the database stored in the memory 130. In various embodiments, the object recognizer 222 may obtain association information on food associated with the object. For example, the object recognizer 222 may obtain parameters for obtaining information on calories per unit of the food associated with the object or information on ingredients (e.g., carbohydrates, protein, fats, and vitamins) of the food. For example, the object recognizer 222 may recognize that the object is associated with the food using a wavelength associated with the object. In various embodiments, to obtain this information, the processor 120 may retrieve the database including data associated with food stored in the memory 130 or may perform signaling with an external electronic device (e.g., a big data server) on the basis of data obtained by the object recognizer 222. The processor 120 may obtain ingredients (or nutrients) of the food using a table in the database of the electronic device 101 or a table in a database stored in the external electronic device at least on the basis of the retrieval or signaling.

In various embodiments, the voice recognizer 224 may recognize a voice command that is received while acquiring the image or is received within a specified time after acquiring the image. For example, the voice recognizer 224 may receive the voice command using a microphone (or transducer) while acquiring the image or within the specified time after acquiring the image. The voice recognizer 224 may recognize the voice command through the retrieval of a database associated with voice recognition stored in the memory 130 or through signaling with an external electronic device (e.g., a voice recognition server). When it is identified that the recognized voice command is associated with the image, the voice recognizer 224 may provide information on the voice command to various components associated with the processor 120 (e.g., components in the image processing module, the biometric information processing module 240, and the rendering module 270).

In various embodiments, the biometric information processing module 240 may process biometric information on a user. In various embodiments, the biometric information may be obtained via the sensor module 176 included in the electronic device 101. In various embodiments, the biometric information may be obtained from another electronic device (e.g., a wearable device), such as the electronic device 102 linked with the electronic device 101, which is shown in FIG. 1. In various embodiments, the biometric information processing module 240 may include a food manager 242, a scheduler 244, and a user profile database 246.

In various embodiments, the food manager 242 may include a database associated with food 243. In various embodiments, the database associated with the food 243 may be obtained via a server or the like. In various embodiments, the database associated with the food may be recorded or updated by the user using the electronic device 101. In various embodiments, the database associated with the food 243 or instructions (or programs) associated with the database may refer a food intelligent agent. In various embodiments, the food intelligent agent may be used to configure or use the database associated with the food 243.

In various embodiments, the food manager 242 may provide information on food using the database.

In various embodiments, the scheduler 244 may generate a schedule for a food type or food intake for a user associated with the electronic device 101 on the basis of association information on food associated with an object recognized by the image processing module 210. In various embodiments, the scheduler 244 may obtain, as the association information, at least one of information on calories per unit of food associated with an object or information on ingredients of the food from the object recognizer 222. The scheduler 244 may identify what kind of food is adequate for physical characteristics (e.g., weight, height, age, eating habits, and body fat level) of the user or may identify the amount of intake adequate for the physical characteristics of the user at least on the basis of the association information.

In various embodiments, the scheduler 244 may process the identified association information on the basis of the physical characteristics of the user or the biometric information on the user. For example, the scheduler 244 may generate information on the calories of food that the user eats, a certain nutrient, or information for guiding the intake of food containing a certain nutrient at least on the basis of information on the kind of food adequate for the physical characteristics of the user or the amount of intake adequate for the physical characteristics of the user. The scheduler 244 may display the generated information through the display device 160 in association with the rendering module 270.

In various embodiments, the user profile database 246 may store the biometric information on the user associated with the electronic device 101. In various embodiments, the biometric information may include health information, such as the user's height, weight, blood pressure, and blood sugar level. In various embodiments, the biometric information may be obtained from an external server (e.g., a server associated with a hospital, a health center, and the like). In various embodiments, the biometric information may be updated by at least one sensor of the electronic device 101. For example, the biometric information may be updated at least on the basis of food eaten by the user associated with the electronic device 101 and calories consumed by the user exercising or the like. For example, the user profile database 246 may store data that is generated on the basis of at least one of the biometric information on the user obtained through the sensor module 176 and biometric information on the user obtained through a sensor module of another electronic device (e.g., a wearable device) and received from the other electronic device. For example, the data stored in the user profile database 246 may include information on a change in the weight of the user, information on the amount of food eaten by the user, and the like. The user profile database 246 may interwork with other components (e.g., the image processing module 210 and the biometric information processing module 240) in the electronic device 101 in order to provide the data stored in the user profile database 246. In various embodiments, the processor 120 may obtain information on food intake from the user profile database 246.

In various embodiments, the rendering module 270 may display at least one of information obtained through the image processing module 210 and information obtained through the biometric information processing module 240 via the display device 160. In various embodiments, the rendering module 270 may display the information obtained through the image processing module 210 within a user interface associated with an application (e.g., Bixby™) for providing an artificial intelligence service. In various embodiments, the rendering module 270 may display the information obtained through the image processing module 210 within a notification area or notification bar. In various embodiments, the rendering module 270 may display the information obtained through the image processing module 210 within a user interface associated with a health application (e.g., Samsung (S) Health™). In various embodiments, the rendering module 270 may display the information obtained through the biometric information processing module 240 within a user interface associated with an application (e.g., Bixby™) for providing an artificial intelligence service. In various embodiments, the rendering module 270 may display the information obtained through the biometric information processing module 240 within a notification area or notification bar. In various embodiments, the rendering module 270 may display the information obtained through the biometric information processing module 240 within a user interface associated with a health application (e.g., Samsung (S) Health™).

The electronic device 101 (or the processor 120) shown in FIG. 2 may perform operations described below with reference to FIGS. 4 to 21.

Figure 3:
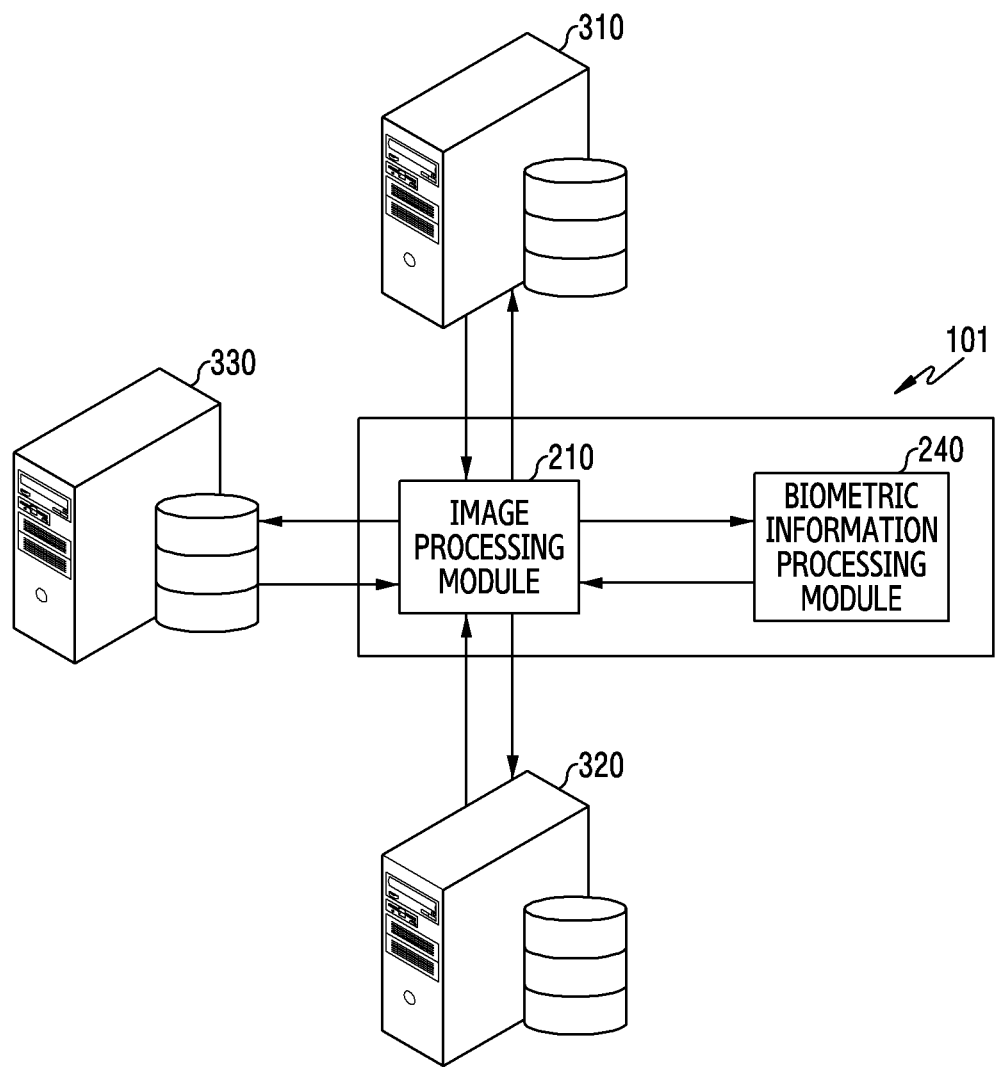
FIG. 3 illustrates an example of signaling between an electronic device and an external electronic device according to various embodiments.

FIG. 3 illustrates an example of signaling between an electronic device and an external electronic device according to various embodiments. This signaling may occur between the electronic device 101 shown in FIG. 1 or the electronic device 101 shown in FIG. 2 and the external electronic device (e.g. the electronic device 102, the electronic device 104, or the server 108) shown in FIG. 1.

Referring to FIG. 3, the image processing module 210 of the electronic device 101 may identify an object associated with food from an image obtained by the camera module 180. The image processing module 210 may interwork with the communication module 190 to transmit information on the object (or information on the image including the object) to an external electronic device 310. In various embodiments, the external electronic device 310 may be a server that recognizes the object included in the image. In various embodiments, the external electronic device 310 may identify which food the object is associated with at least on the basis of the received information on the object. The external electronic device 310 may provide information on food identified as being associated with the object to the image processing module 210. For example, the information on the food may include data on the type of the food and data on nutrients of the food.

In various embodiments, the image processing module 210 may interwork with the communication module 190 to transmit the information on the image, the information on the object, or information on the type of the food to an external electronic device 320. In various embodiments, the external electronic device 320 may be a server that provides additional information on the food associated with the object included in the image. In various embodiments, the external electronic device 320 may identify additional information on the food at least on the basis of the received information. In various embodiments, the additional information may refer to the food, nutrients of the food, or the calories of the food. In various embodiments, the additional information may refer to a recipe for the food or a shopping guide for a semi-prepared food associated with the food.

In various embodiments, the additional information may refer to information on other food associated with the food. For example, the external electronic device 320 may identify, as the additional information, information on another food associated with the food or information on a recipe for the food or the other food at least on the basis of the received information. In various embodiments, the other food may refer to a food that can provide nutrients that are different from the nutrients of the food. In various embodiments, the other food may refer to a food that can provide nutrients similar to the nutrients of the food.

The external electronic device 320 may provide the additional information to the image processing module 210. The image processing module 210 may process the additional information using various methods. For example, the image processing module 210 may display the additional information through a user interface of a health application, a user interface associated with a web page, a user interface associated with video playback, and the like.

In various embodiments, the image processing module 210 may transmit at least one of the information on the food associated with the object and the additional information on the food to an external electronic device 330. The external electronic device 330 may be a server that configures big data associated with food. In various embodiments, the external electronic device 330 may refer to a server that receives information on food from not only the electronic device 101 but also other electronic devices and configures big data on the basis of the received information. Upon receiving a request from a device, such as the electronic device 101, the external electronic device 330 may transmit the information on the food or the additional information on the food to the device.

In various embodiments, the image processing module 210 may provide the biometric information processing module 240 with at least one of information associated with food processed by the image processing module 210, information associated with food obtained from the external electronic device 310, information associated with food obtained from the external electronic device 320, and information associated with food transmitted to or received from the external electronic device 330 (not shown in FIG. 3). For example, the image processing module 210 may provide this information to the biometric information processing module 240 in order to link the information with biometric information on a user.

In various embodiments, the biometric information processing module 240 may process the information. In various embodiments, the biometric information processing module 240 may process the information on the basis of biometric information on a user, such as physical characteristics of the user. For example, the biometric information processing module 240 may store the information in order to monitor the user's eating habits. In another example, the biometric information processing module 240 may generate association information that associates the biometric information on the user obtained by the biometric information processing module 240 with the information and may display or store the association information. The information processed or handled by the biometric information processing module 240 may be provided to the user through various methods (e.g., by providing a notification).

FIG. 3 illustrates an example where the external electronic device 310, the external electronic device 320, and the external electronic device 330 are independently configured, which is for the convenience of explanation. According to an embodiment, at least one or more of the external electronic device 310, the external electronic device 320, and the external electronic device 330 may be configured as a single electronic device.

Figure 4:
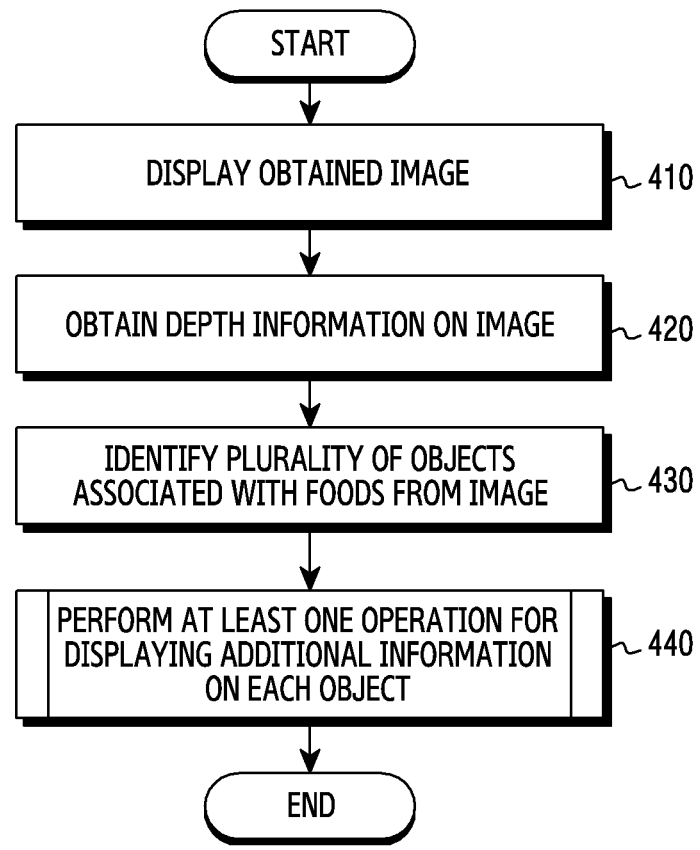
FIG. 4 illustrates an example of the operation of an electronic device according to various embodiments.

FIG. 4 illustrates an example of the operation of an electronic device according to various embodiments. This operation may be performed by the electronic device 101 shown in FIG. 1, the electronic device 101 shown in FIG. 2, the processor 120 of the electronic device 101 shown in FIG. 1, or the processor 120 of the electronic device 101 shown in FIG. 2.

Referring to FIG. 4, in operation 410, the processor 120 may display an image obtained by a camera module 180. In various embodiments, the image may be obtained by at least one camera included in the camera module 180. For example, the image may be an image obtained by a first camera of the at least one camera (e.g., of one or more cameras), an image obtained by a second camera having a different characteristic from that of the first camera of the at least one camera, or an image obtaining by compositing a first image obtained by the first camera and a second image obtained by the second camera. In various embodiments, the view of the first camera may include a disparity (or parallax) relative to the view of the second camera. For example, the disparity may correspond to a disparity between the left eye of a person and the right eye of the person. Using the disparity, the processor 120 may obtain depth information on the image obtained by compositing the first image and the second image. In various embodiments, the image may be associated with food. In various embodiments, the image may include objects associated with the food. For example, the image may be an image obtained by photographing food.

In operation 420, the processor 120 may obtain depth information on the image. In various embodiments, the depth information may be obtained on the basis of at least one light emitted from the electronic device 101 while obtaining the image. The at least one light may be emitted in a direction corresponding to the view (e.g., Field Of View "FOV" or Angle Of View "AOV") of the at least one camera. In various embodiments, the depth information may be obtained through cameras having different characteristics (e.g., the first camera and the second camera). In various embodiments, the depth information may be obtained through post-processing of the obtained image. In various embodiments, the depth information may be used to identify the amount of each of the foods (e.g., the volume of each piece of food and/or the mass of each piece of food) associated with the objects included in the image.

In operation 430, the processor 120 may identify objects associated with food from the image. In various embodiments, the processor 120 may extract at least one feature from the image. The processor 120 may identify that the image is associated with the food on the basis of the at least one feature. In various embodiments, the processor 120 may identify that the image is associated with the food on the basis of training data. In various embodiments, the training data may be obtained on the basis of an artificial intelligence algorithm, such as machine learning, neural network, or deep learning algorithms. The training data may be used for reference as learning data. On the basis of this identification, the processor 120 may obtain, through image processing, information on a boundary of each of a plurality of objects in the image, information on a surface of each of the plurality of objects, information on the curvature of each of the plurality of objects, or information on a texture associated with the plurality of objects, thereby identifying the objects associated with the food from among the plurality of objects. In various embodiments, the processor 120 may divide the objects from the image. For example, the processor 120 may divide the objects from the image in order to recognize each of the objects.

In operation 440, the processor 120 may perform at least one operation for displaying additional information on each of the objects. In various embodiments, the additional information may include data on a result of recognizing each of the objects. In various embodiments, the processor 120 may perform the at least one operation in order to obtain various kinds of additional information obtained by recognizing the objects associated with each of the food. The at least one operation may refer to an operation utilized to intuitively provide the additional information associated with the food. In various embodiments, the at least one operation will be described later with reference to FIGS. 5 to 21.

Figure 5:
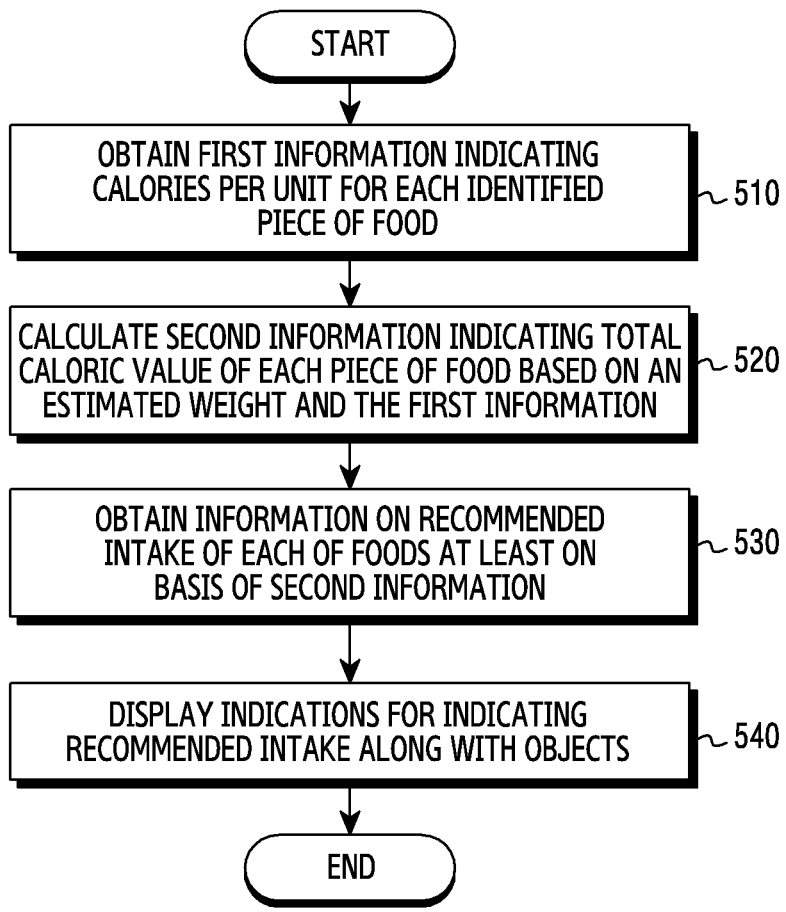
FIG. 5 illustrates an example of the operation of an electronic device displaying indications about objects associated with food according to various embodiments.

FIG. 5 illustrates an example of the operation of an electronic device displaying indications about objects associated with food according to various embodiments. This operation may be performed by the electronic device 101 shown in FIG. 1, the electronic device 101 shown in FIG. 2, the processor 120 of the electronic device 101 shown in FIG. 1, or the processor 120 of the electronic device 101 shown in FIG. 2.

Operations 510 to 540 in FIG. 5 may be associated with operation 440 in FIG. 4.

Referring to FIG. 5, in operation 510, the processor 120 may obtain caloric information (e.g., "first information) including, for example, a number of calories per unit (e.g., weight) of each of food item at least on the basis of information on each of the objects. In various embodiments, the processor 120 may identify the objects associated with the food from the image through an operation, such as operation 430 in FIG. 4. In various embodiments, the processor 120 may recognize each of the objects at least on the basis of information on each of the objects. For example, the processor 120 may retrieve a database stored in the memory 130 using the information on each of the objects including data on a texture, a boundary, or a surface of each of the objects (e.g., such as by visual imagery or other such data), thereby recognizing which food the objects correspond to (e.g., by algorithmic comparison resulting in a predetermined threshold level of visual similarity). The processor 120 may retrieve the database stored in the memory 130, may retrieve a server linked with the electronic device 101, or may retrieve a web page on the basis of the recognition result, thereby obtaining the first information on the calories per unit (e.g., calories per 100 g and calories per serving portion) of each of the food associated with the respective objects. In another example, the processor 120 may transmit information on the identified objects to an external electronic device (e.g., a server) that is associated with image recognition and is linked to the electronic device 101. Upon receiving the information on the objects, the external electronic device can recognize which food the objects correspond to. The external electronic device may transmit information on the recognition result to the electronic device 101. The processor 120 may retrieve the database stored in the memory, may retrieve a server (which may be the same as or different from the external electronic device) linked with the electronic device 101, or may retrieve a web page on the basis of the received information, thereby obtaining the first information on the calories per unit of each of the food associated with the respective objects.

In operation 520, the processor 120 may calculate caloric information (e.g., "second information") indicating the total estimated calories included in each of the food pieces based on at least the depth information and the first information. In various embodiments, the processor 120 may obtain the second information at least on the basis of data on the calories per unit of each of the food included in the first information and data on the amount of each of the food obtained through the depth information. For example, when the calories per unit of food A included in the first information is identified to be 114 kcal/100 g, and the amount of food A included in the depth information is estimated to be 600 g, the processor 120 may calculate the total calories of food A to be 684 kcal. The processor 120 may calculate the second information including data indicating that the estimated total caloric value of food A is 684 kcal. In another example, when the calories per unit of food B included in the first information is 319 kcal/100 g and the amount of food B included in the depth information is estimated to be 1000 g, the processor 120 may calculate that the total estimated caloric value of food B is 3188.56 kcal. The processor 120 may thereby calculate the second information including data indicating that the total calories of food B is 3188.56 kcal.

In operation 530, the processor 120 may obtain information on the recommended intake of each of the food at least on the basis of the second information. The processor 120 may calculate total calories in the case of eating all the food on the basis of the second information on the total calories of each of the food associated with the respective objects included in the image. Referring to the foregoing examples, the processor 120 can add the total calories of food A, which are 684 kcal, and the total calories of food B, which are 3188.56 kcal, thereby calculating the total calories of 38729.56 kcal in the case of eating all of these food. The processor 120 may obtain the information on the recommended intake of each of the food at least on the basis of information on the calculated total calories.

In various embodiments, the processor 120 may obtain information on the recommended intake of each of the food at least on the basis of the second information and biometric information of a user associated with the electronic device 101. The biometric information may be stored in the electronic device 101 or in a server linked with the electronic device 101.

For example, the processor 120 may obtain information on the recommended intake of each of the food at least on the basis of the information on the calculated total calories and information on a food intake history of the user associated with the electronic device 101. Specifically, when the food intake history indicates that the user consumes more carbohydrates than fats or protein and a pre-loaded guideline for a recommended food intake indicates fats and proteins should be consumed in a higher quantity than carbohydrates, the processor 120 may set the recommended intake of food to suggest a higher consumption of fats or protein and a reduction in the consumption of carbohydrates. Alternatively, when the food intake history indicates that the user overate at a previous meal resulting in a present or potential excess consumption of calories for a given period of time, the processor 120 may generation a notification recommending a reduction in a present consumption of food, to equalize to a reference recommended intake. The processor 120 may obtain information on the recommended intake of each of the food on the basis of the identified total recommended intake.

In another example, the processor 120 may obtain information on the recommended intake of each of the food at least on the basis of the information on the calculated total calories and information on a medical history of the user. Specifically, when the information on the medical history indicates that the user is diabetic, the processor 120 may identify the recommended intake of food with a high sugar level to be lower than a reference recommended intake and may identify the recommended intake of food with a low sugar level to be lower than a reference recommended intake. The processor 120 may obtain information on the recommended intake of each of the food on the basis of the identification result.

In still another example, the processor 120 may receive information on a ratio associated with nutrients and may obtain information on the recommended intake of each of the food on the basis of this information. Specifically, the processor 120 may receive an input of a ratio associated with nutrients to set the ratio of protein to 80% and the respective ratios of carbohydrates and fats to 10%. For example, the processor 120 may obtain information on high-protein food and low-carbohydrate food among the plurality of food on the basis of nutrients of each of the plurality of food.

In yet another example, the processor 120 may obtain information on the recommended intake of each of the food on the basis of the information on the calculated total calories and information on the user's exercise history. For example, when the information on the exercise history indicates that the user does exercise to burn many calories during a specified time period, the processor 120 may identify the total recommended intake to be a higher value than a recommended intake per meal. The processor 120 may obtain information on the recommended intake of each of the food on the basis of the identified total recommended intake.

In still another example, the processor 120 may obtain information on the recommended intake of each of the food on the basis of the information on the calculated total calories and nutrients (e.g., carbohydrates, fats, protein, vitamins, and the like) of each of the food.

In yet another example, the processor 120 may obtain information on the recommended intake of each of the food on the basis of the information on the calculated total calories and the user's stress index.

Although it has been described that the processor 120 according to various embodiments may obtain information on the recommended intake of each of the food on the basis of information on the user's physical feature, the information on the exercise history, the information on the calculated total calories, information on the nutrients of each of the food, the stress index, and the information on the user's medical history, the present disclosure is not limited thereto.

In operation 540, the processor 120 may display indications for indicating the recommended intake along with the objects (as will be illustrated below).

For example, the indications indicating the recommended intake may include display of at least one of a number and a letter indicating the recommended intake. Each of the indications configured with at least one of the number and the letter may be displayed near each of the objects for association with each of the objects associated with the food. For example, each of the indications configured with at least one of the number and the letter may be superimposed (or partially superimposed) on each of the objects. Alternatively, each of the indications configured with at least one of the number and the letter may be displayed within each of the objects. Alternatively, each of the indications configured with at least one of the number and the letter may be displayed within a specified distance from each of the objects. However, the present disclosure is not limited thereto.

In another example, each of the indications for indicating the recommended intake may be displayed by highlighting a portion of an object corresponding to the recommended intake relative to another portion of the object. For example, referring to FIG. 6, a partial image 600 may include an indication 620, which may take the form of a visual outline surrounding an identified food item. The processor 120 may display the indications 620 superimposed on an object 610 associated with a particular piece of food (e.g., pork cutlet) identified in the partial image 600. The user may recognize the recommended intake of the food (e.g., pork cutlet) through the difference in size between the indication 620 and the object 610. In various embodiments, the processor 120 may further include another indication 630 providing further information on the recommended intake in the partial image 600, such as an estimated caloric value. The indication 630 may be configured with a combination of numbers or letters in order to explicitly provide the recommended intake in the form of, for example, an estimated caloric value.

Figure 6:
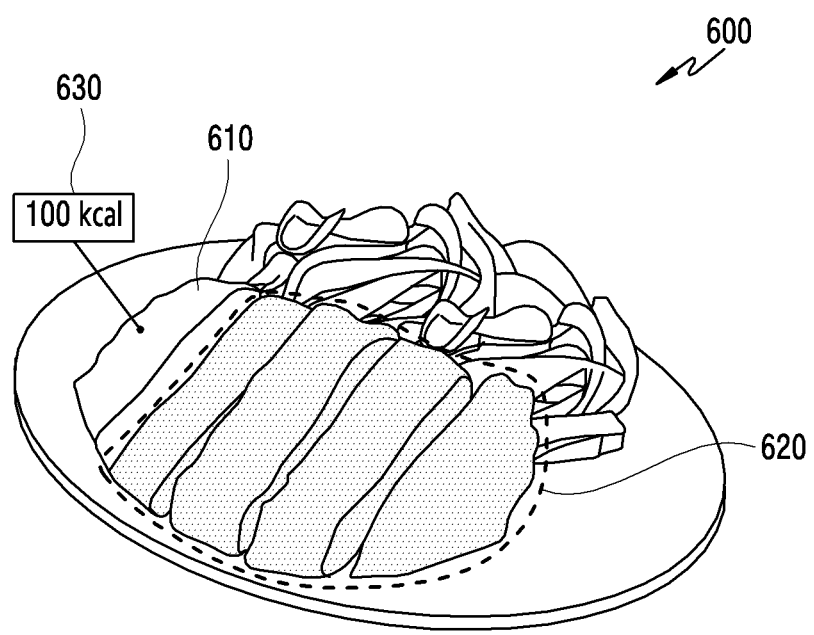
FIG. 6 illustrates an example of an image displayed on an electronic device according to various embodiments.
Figure 7:
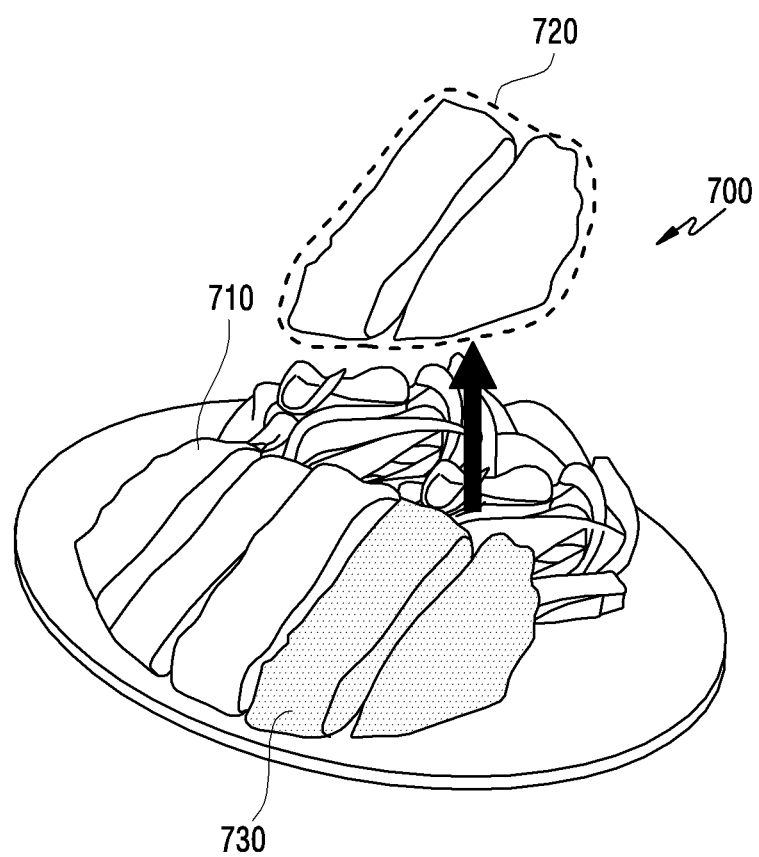
FIG. 7 illustrates another example of an image displayed on an electronic device according to various embodiments.

FIG. 6 shows an example of visually providing an example indication 630. In various other embodiments, the indication 630 may be output through a sound, such as a voice notification. In various other embodiments, the indication 630 may be output using a haptic effect. However, the present disclosure is not limited thereto.

In still another example, each of the indications indicating the recommended intake may be configured to be displayed with a shape of at least a portion of the objects. For example, referring to FIG. 7, a partial image 700 may include an indication 720 including an outline of a portion of food and a reproduction image of a portion of food 730. The processor 120 may display a representation of a portion of an object 710 associated with food in the partial image 700 as the indication 720. For example, the processor 120 may extract a portion 730 having a size corresponding to the recommended intake from the object 710 in the partial image 700. The processor 120 may display the portion of the object 710 corresponding to the recommended intake using the indication 720. In various embodiments, the indication 720 may be displayed as "floating" near the object 710. In various embodiments, the processor 120 may control the transparency of the portion of the object 710 based on the recommended intake, so as to display floating of the indication 720. For example, the processor 120 may semi-transparently display a region 730 corresponding to the portion of the object 710 corresponding to the recommended intake.

Figure 8:
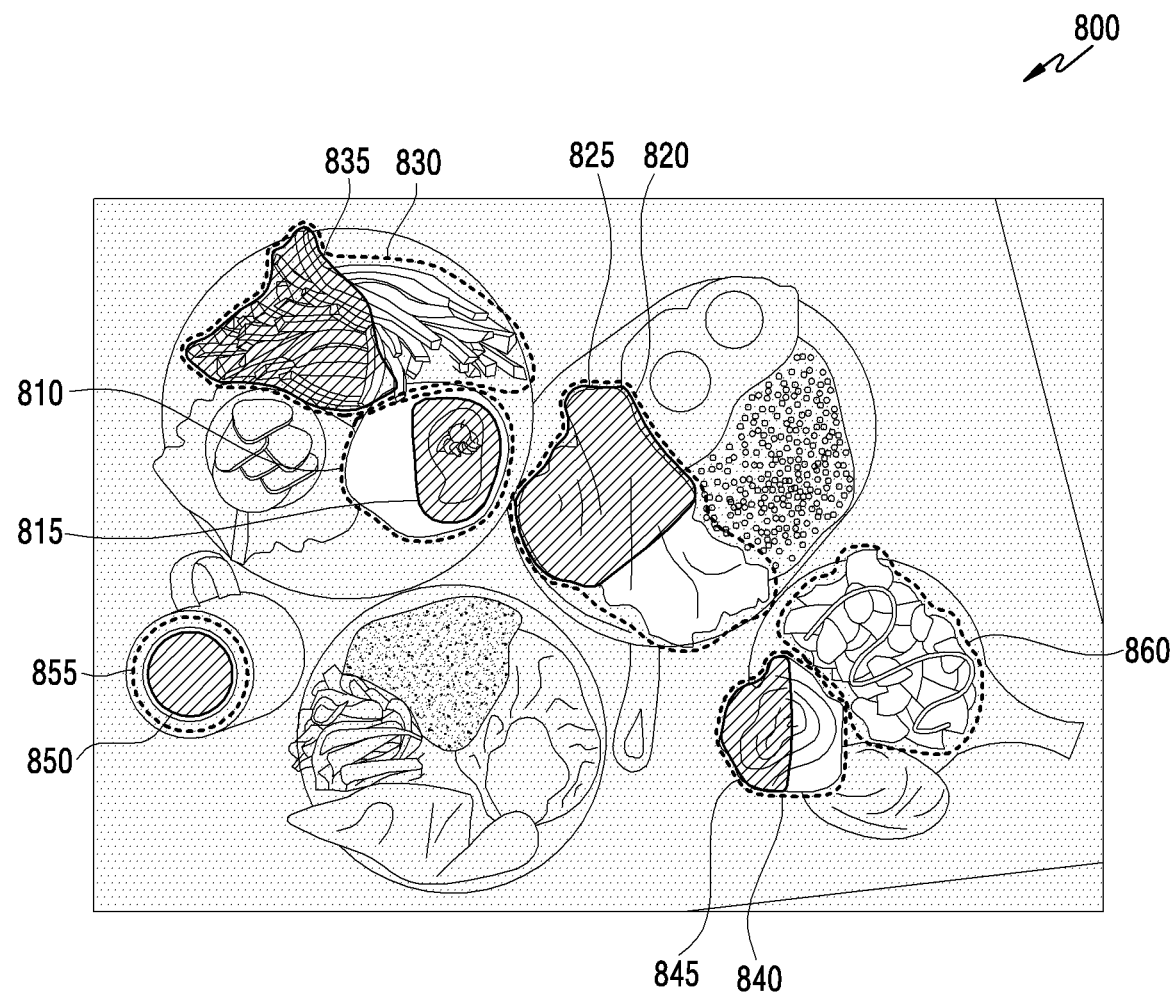
FIG. 8 illustrates still another example of an image displayed on an electronic device according to various embodiments.

In various embodiments, the processor 120 may display each of the indications along with each of the objects. For example, referring to FIG. 8, the processor 120 may display an image 800. The image 800 may include indicator display objects associated with food included in the image 800. For example, the image 800 may include an object 810 indicating a hamburger, an object 820 indicating a steak, an object 830 indicating French fries, an object 840 indicating bread, an object 850 indicating a cafe latte, and an object 860 indicating a ricotta cheese salad. The image 800 may include indications associated with at least some of the objects. For example, the image 800 may include an indication 815 associated with the object 810, an indication 825 associated with the object 820, an indication 835 associated with the object 830, an indication 845 associated with the object 840, and an indication 855 associated with the object 850. The indication 815, the indication 825, the indication 835, the indication 845 and the indication 855 may indicate the recommended intake of the food associated with the object 810, the object 820, the object 830, the object 840, and the object 850, respectively. For example, the area of the indication 815 may correspond to the recommended intake portion of the hamburger, the area of the indication 825 may correspond to the recommended intake portion of the steak, the area of the indication 835 may correspond to the recommended intake portion of French fries, the area of the indication 845 may correspond to the recommended intake portion of the bread, and the area of the indication 855 may correspond to the recommended intake portion of the coffee. As shown in FIG. 8, the object 860 may not be associated with an indication. For example, when the user is allergic to cheese, the processor 120 may set the recommended intake of cheese-containing food to a value of "0" (e.g., in operation 530 of obtaining the information on the recommended intake of each of the food), thereby preventing the user from eating food to which the user is allergic.

In some embodiments, the processor 120 may blur an object which does not match a user's preference, or is associated with food not obtained through object recognition among a plurality of objects associated with a plurality of food as in the image 800. For example, as shown in FIG. 8, the processor 120 may blur objects other than the objects 810, 820, 830, 840, 850, and 860 in the image 800.

FIG. 8 shows one example among the methods for displaying objects and indications, and the electronic device 101 according to various embodiments may display at least one of the objects or the indications using various methods. For example, the processor 120 of the electronic device 101 according to various embodiments may deactivate an object associated with food known to be harmful to the user, or may display a visual object indicating an alert so that the harmful food is selected. In another example, the processor 120 of the electronic device 101 according to various embodiments may set display of visual effects such as the texture, the color, or the brightness of each of the objects associated with each of the food to different levels, depending on nutrients of each of the food so that the user can recognize the nutrients of each of the food. For example, the processor 120 may display a food having carbohydrates as a main nutrient with an effect having a first color and may display a food having protein as a main nutrient with an effect having a second color. However, the present disclosure is not limited thereto.

As described above, the electronic device 101 (or the processor 120) according to various embodiments may show a visual effect associated with Augmented Reality (AR) in a preview image displayed within a user interface and obtained via a camera, thereby intuitively guiding the user on the intake of food. In various embodiments, the electronic device 101 may display an indication for the visual effect associated with AR so that the user can intuitively a recommended intake.

Figure 9:
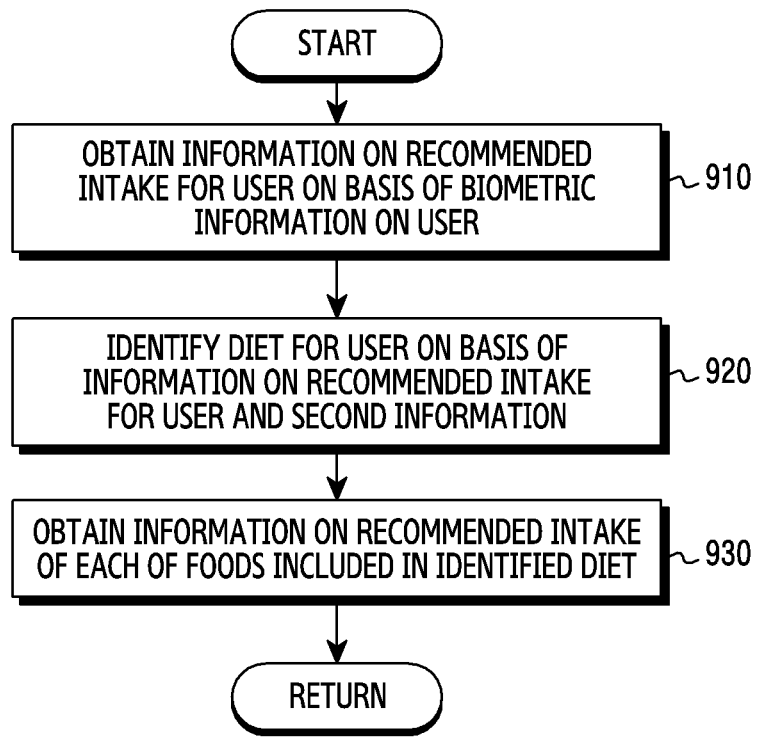
FIG. 9 illustrates an example of the operation of an electronic device obtaining information on the recommended intake of each food according to various embodiments.

FIG. 9 illustrates an example of the operation of an electronic device obtaining information on the recommended intake of each food according to various embodiments. This operation may be performed by the electronic device 101 shown in FIG. 1, the electronic device 101 shown in FIG. 2, the processor 120 of the electronic device 101 shown in FIG. 1, or the processor 120 of the electronic device 101 shown in FIG. 2.

Operations 910 to 930 in FIG. 9 may be associated with operation 530 in FIG. 5.

Referring to FIG. 9, in operation 910, the processor 120 may obtain information on a recommended intake for the user on the basis of biometric information on the user. In various embodiments, the biometric information may include at least one of a medical history of the user, a food intake history of the user, and an exercise history of the user. In various embodiments, the biometric information may include at least one of information on a diet taken by the user, information on a health program or exercise program performed by the user, and information on the user's exercise level. FIG. 9 shows an example in which the processor 120 obtains the information on the recommended intake for the user on the basis of the biometric information, which is for the convenience of explanation. In various embodiments, the processor 120 may obtain information on a recommended intake for the user on the basis of other information associated with food, which is different from the biometric information. In some embodiments, the processor 120 may obtain information on a recommended intake for the user on the basis of information on the user's setting associated with a diet. For example, when the information on the user's setting indicates that the user provides a high-protein diet, the processor 120 may identify information on a recommended intake for the user so that the user takes in protein-based nutrients. In some other embodiments, the processor 120 may obtain information on a recommended intake for the user on the basis of time information. For example, when a time period measured by the electronic device 101 is evening, the processor 120 may identify information on a recommended intake for the user so that the user takes in low-carbohydrate-based nutrients.

In operation 920, the processor 120 may identify (or generate) a dietary plan for the user on the basis of the information on the recommended intake for the user and the second information. For example, the processor 120 may identify a dietary plan for the user on the basis of a combination of food excluding food allergic to the user. In another example, the processor 120 may identify a dietary plan for the user on the basis of food corresponding to a main dish among the food associated with the objects included in the image. In still another example, the processor 120 may identify a dietary plan for the user on the basis of the user's preference. In yet another example, when the user excessively takes in carbohydrates and sodium in the afternoon, the processor 120 may identify a dietary plan for the user on the basis of low-carbohydrate and low-sodium food. In still another example, when the user is already on a diet, the processor 120 may identify a dietary plan for the user on the basis of food with low calories.

In operation 930, the processor 120 may obtain information on the recommended intake of each of food included in the identified dietary plan. For example, the processor 120 may divide the recommended intake for the user by each of the food included in the diet, thereby obtaining the information on the recommended intake of each of the food.

As described above, the electronic device 101 according to various embodiments may identify a diet for the user at least on the basis of the user' preference, the biometric information on the user, and the user's setting and may identify the recommended intake of each of food included in the identified diet, thereby guiding the user on the intake of a balanced diet.

Figure 10:
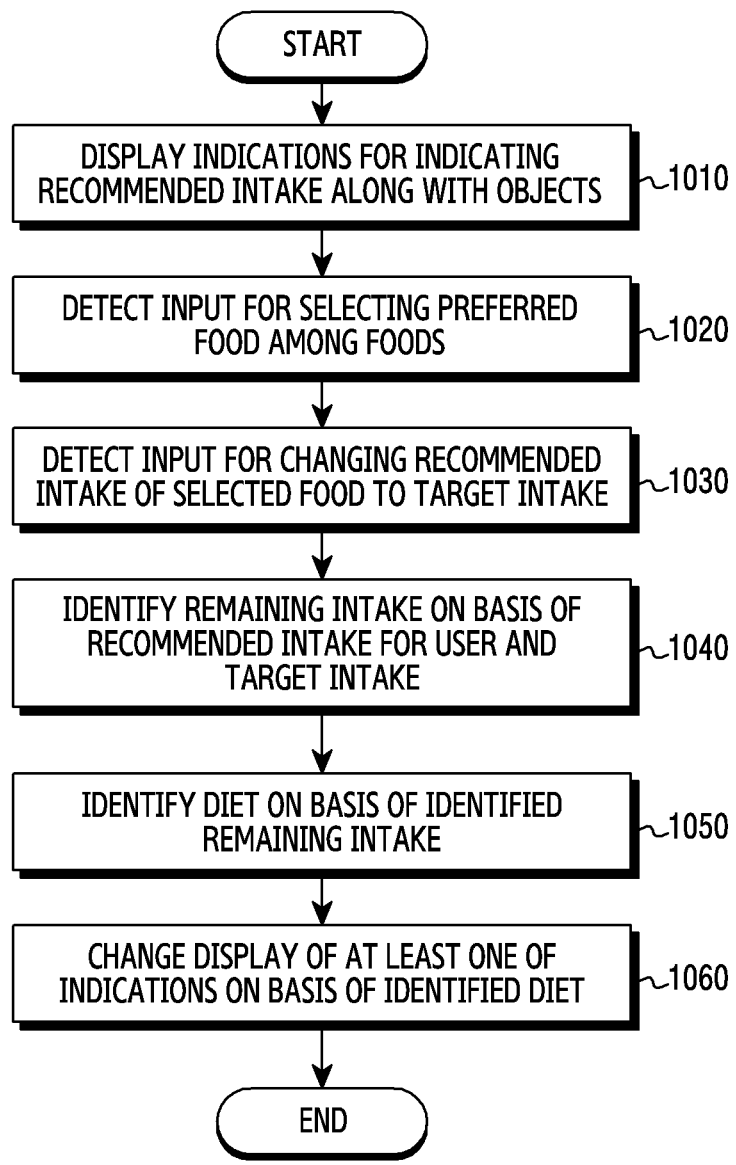
FIG. 10 illustrates an example of the operation of an electronic device changing a display of an indication according to various embodiments.

FIG. 10 illustrates an example of the operation of an electronic device changing a display of an indication according to various embodiments. This operation may be performed by the electronic device 101 shown in FIG. 1, the electronic device 101 shown in FIG. 2, the processor 120 of the electronic device 101 shown in FIG. 1, or the processor 120 of the electronic device 101 shown in FIG. 2.

Referring to FIG. 10, in operation 1010, the processor 120 may display visual indications helping to indicate a recommended intake along with objects. In various embodiments, operation 1010 may for example correspond to operation 540 (and as further illustrated in FIGS. 6, 7 and 8).

In operation 1020, the processor 120 may detect an input for selecting preferred food among food. For example, the input may include a single-tap input, a double-tap input, a drag input, a force-touch input, a long-press input, and/or a hovering input. In various embodiments, the input may include an input for selecting at least one object among the displayed objects. In various embodiments, the input may include an input for selecting at least one indication among the indications. In various embodiments, the input may correspond to a voice command of a user input through a microphone (or transducer). The input may include a voice command to refer to at least one of the objects. For example, the input may include a word (e.g., "pork cutlet") corresponding to one of the plurality of food or a sentence including the word (e.g., "I will have the pork cutlet").

In various embodiments, the processor 120 may display information for changing the recommended intake of the selected food to a target intake in response to the detection of the input.

Figure 11:
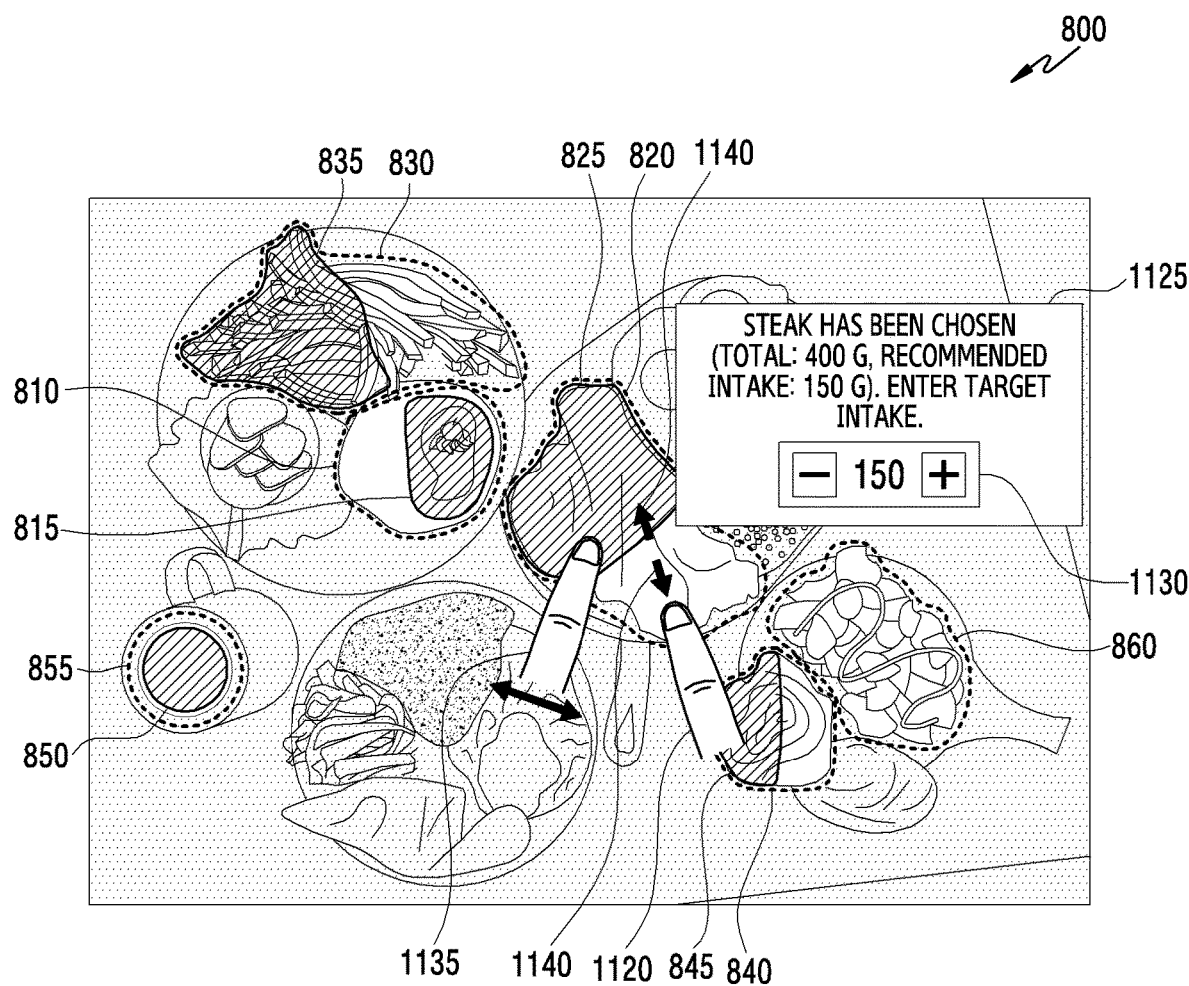
FIG. 11 illustrates yet another example of an image displayed on an electronic device according to various embodiments.
Figure 12:
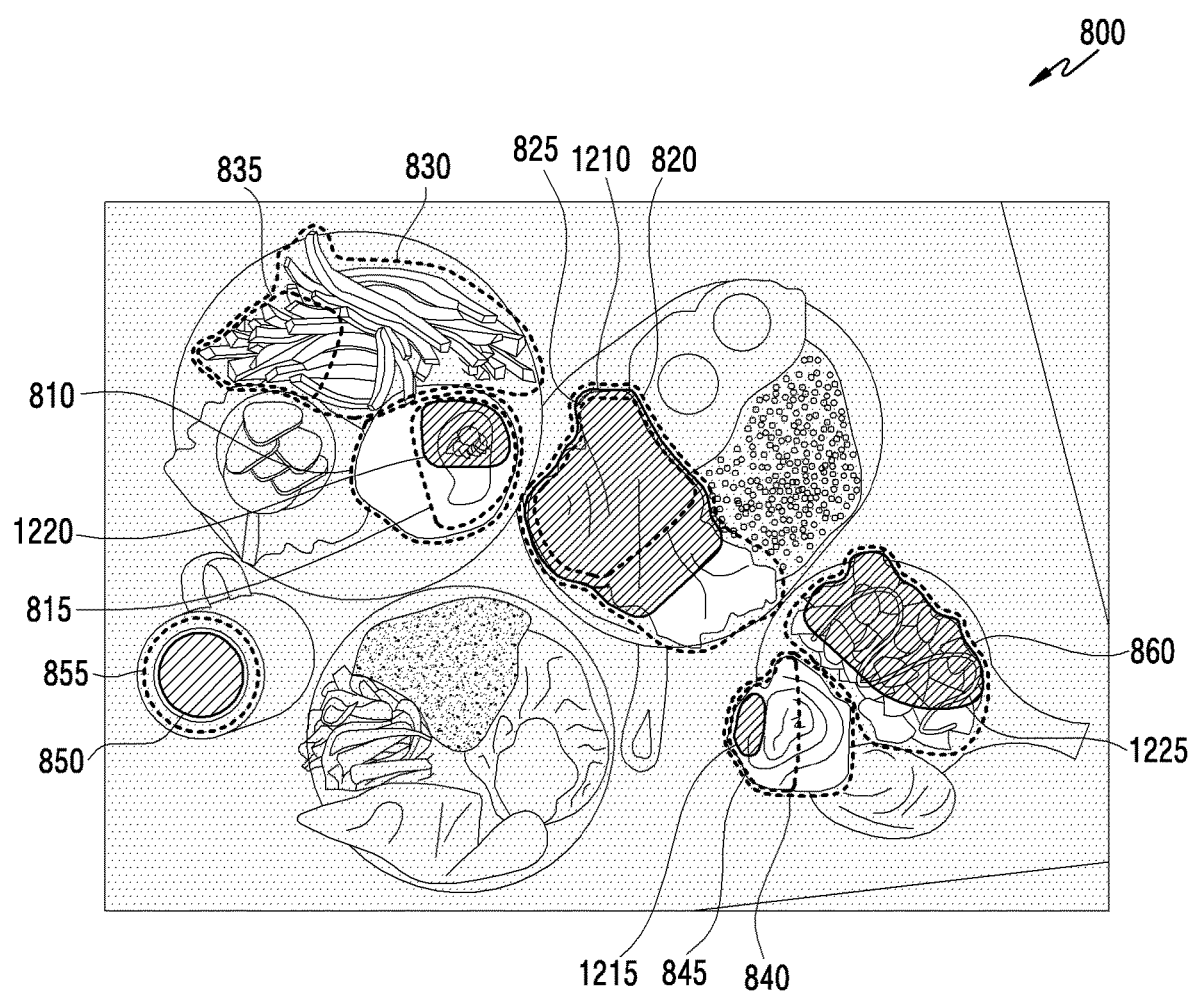
FIG. 12 illustrates still another example of an image displayed on an electronic device according to various embodiments.

For example, referring to FIG. 11, the processor 120 may display a window 1125 that is superimposed on an image 800 in response to the detection of an input 1120 for an object 820 or an indication 825. The window 1125 may include at least one visual object 1130 for changing the recommended intake to the target intake.

In another example, referring to FIG. 11, the processor 120 may display at least one visual object 1140 that is superimposed on the image 800 in response to the detection of an input 1135 for the object 820 or the indication 825. The at least one visual object 1140 may be displayed within the image 800 to change the recommended intake to the target intake.

In operation 1030, the processor 120 may detect an input for changing the recommended intake of the selected food to a new target intake. In various embodiments, the new target intake may be distinguished from the recommended intake. In various embodiments, the new target intake may refer to the intake of particular food, as newly input by the user. For example, referring to FIG. 11, the processor 120 may detect an input for the visual object 1130 displayed in the window 1125. In various embodiments, the input for the visual object 1130 may include an input via at least one button (e.g., a (−) button and a (+) button) included in the visual object 1130. In various embodiments, the input for the visual object 1130 may include an input of a number (150) included in the visual object 1130 using the (−) and (+) buttons, for example. Although not shown in FIG. 11, when the input of the number (150) is detected, the processor 120 may further display a virtual keypad for changing the number. The processor 120 may identify the target intake through a plurality of number keys included in the virtual keypad. In another example, referring to FIG. 11, the processor 120 may detect an input for changing the size (or area) of the indication 825. For example, the input may include a drag input having a direction corresponding to the at least one visual object 1140. In another example, the input may include an input relating to a force touch. In various embodiments, the processor 120 may identify the target intake by identifying a change in pressure caused by the input. In various embodiments, the processor 120 may identify the target intake on the basis of the size of the indication 825 that changes on the basis of the input.

In operation 1040, the processor 120 may identify a remaining intake to be allocated for the user's meal on the basis of the recommended intake for the user and the target intake. For example, the processor 120 may identify the remaining intake to be allocated to the user's meal by subtracting the newly modified target intake from the recommended intake for the user.

In operation 1050, the processor 120 may identify a diet on the basis of the identified remaining intake. In various embodiments, when the target intake is greater than the recommended intake of the selected food, the processor 120 may identify the diet by reducing the recommended intake of at least some of the food included through the display in operation 1010. In various embodiments, when the target intake is greater than the recommended intake of the selected food, the processor 120 may identify the diet by excluding at least some of the food included through the display in operation 1010 and by adding at least one another food. In various embodiments, when the target intake is smaller than the recommended intake of the selected food, the processor 120 may identify the diet by increasing the recommended intake of at least some of the food included through the display in operation 1010. In various embodiments, when the target intake is smaller than the recommended intake of the selected food, the processor 120 may identify the diet by adding at least one another food that is different from the food included through the display in operation 1010.

In operation 1060, the processor 120 may change the display of at least one of the indications on the basis of the identified diet. For example, referring to FIG. 12, the processor 120 may display an indication 1210 within an image 800 to indicate a target intake changed from the recommended intake of steak. Since the indication 1210 indicates the target intake changed from the recommended intake, the indication 1210 may have an area larger than the indication 825. The processor 120 may display, in the image 800, other indications changed due to the target intake changed from the recommended intake. For example, still referring to FIG. 12, the processor 120 may further display, in the image 800, an indication 1215 having a smaller area than an indication 845 indicating the recommended intake of bread. In another example, the processor 120 may further display, in the image 800, an indication 1220 having a smaller area than an indication 815 indicating the recommended intake of a hamburger. In still another example, the processor 120 may add a ricotta cheese salad, which is excluded from the display in operations 540 and 1010, as a diet for the user. The processor 120 may further display an indication 1225 indicating the recommended intake of the ricotta cheese salad within an object 860 associated with the ricotta cheese salad.

As described above, the electronic device 101 according to various embodiments may reconfigure a diet on the basis of an input for changing the recommended intake of a certain food to a target intake and may display the reconfigured diet in an image through a visual effect associated with AR. The electronic device 101 according to various embodiments may guide the user on the intake of food adequate for the user through the display of the visual effect.

Figure 13:
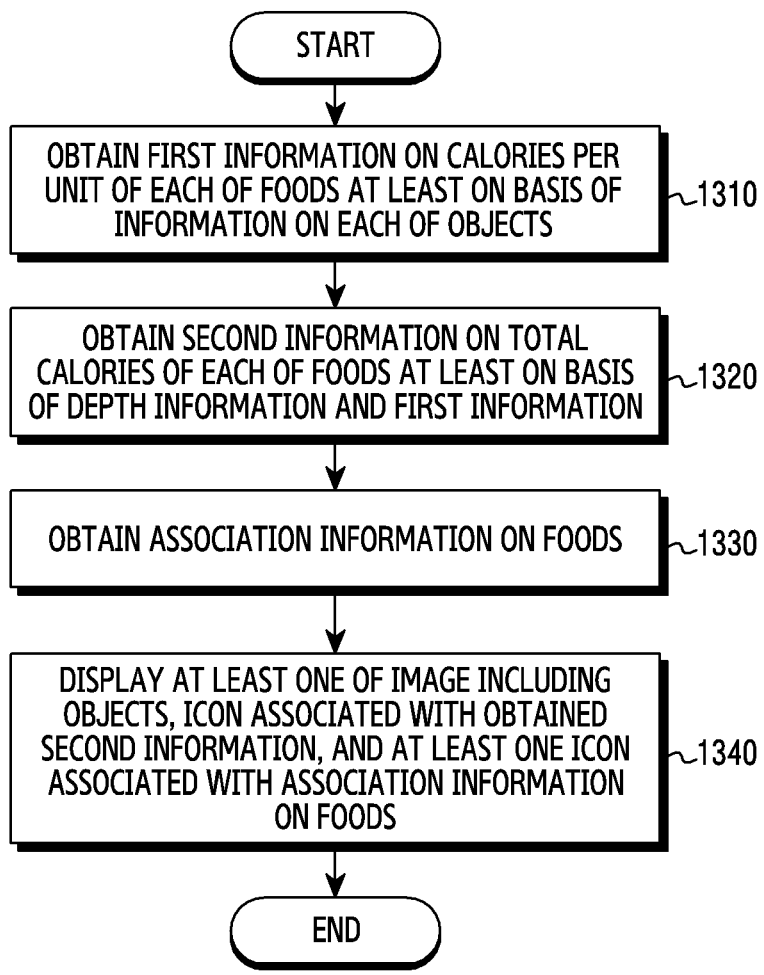
FIG. 13 illustrates an example of the operation of an electronic device displaying objects associated with food along with association information according to various embodiments.

FIG. 13 illustrates an example of the operation of an electronic device displaying objects associated with food along with association information according to various embodiments. This operation may be performed by the electronic device 101 shown in FIG. 1, the electronic device 101 shown in FIG. 2, the processor 120 of the electronic device 101 shown in FIG. 1, or the processor 120 of the electronic device 101 shown in FIG. 2.

Operations 1310 to 1340 in FIG. 13 may be associated with operation 440 in FIG. 4.

Referring to FIG. 13, in operation 1310, the processor 120 may obtain first information on calories per unit of each of the food at least on the basis of information on each of the objects. In various embodiments, operation 1310 may be the same as or similar to operation 510 in FIG. 5.

In operation 1320, the processor 120 may obtain second information on the total calories of each of the food at least on the basis of depth information and the first information. In various embodiments, operation 1320 may be the same as or similar to operation 520 in FIG. 5.

In operation 1330, the processor 120 may obtain association information on the food. In various embodiments, the association information may refer to information derived from the food. For example, the association information may include one or more of the types of nutrients of each of the food, the component ratio of nutrients of each of the food, price information on each of the food, information on nutrients of each of the food, information a place where each of the food is sold, information on other food matching each of the food, information an image (e.g., still image or video) associated with each of the food, webpage information on a place where each of the food is sold, webpage information for uploading an image including the food, and information on an application that is distinguished from another application used to obtain an image including objects associated with the food and is linked to the application. In various embodiments, the association information may be obtained via a database stored in the memory 130 of the electronic device 101 or via a database stored in a server linked with the electronic device 101.

In operation 1340, the processor 120 may display one or more of an image including the objects, an icon associated with the second information, and at least one icon associated with the association information on the food. In various embodiments, the processor 120 may display, along with a user interface that displays the image including the objects associated with the food, the image including the objects, the icon associated with the second information, and the at least one icon associated with the association information on the food in order to provide not only information on the image but also various information related to the food. For example, the processor 120 may obtain the image through a food mode of an application providing an image recognition service or may obtain the image through a normal mode of the application. According to one embodiment, when a feature of the image obtained through the normal mode is extracted and it is determined that the obtained image includes an image of food, the processor 120 may change the operation mode of the application to the food mode. The processor 120 may display the image (e.g., a preview image) obtained through a camera oriented to a region including the food using a user interface of the application. The processor 120 may identify a main subject in the image on the basis of identifying or detecting that the image is fixed (or maintained) for a specified time, may identify a Region Of Interest (ROI) occupied by the main subject, and may track the main subject. The processor 120 may extract the main subject from the image on the basis of tracking and may recognize the extracted main subject, thereby identifying that the objects in the image are associated with the food. Based on the identification, the processor 120 may obtain information on the total calories of the food associated with the objects and may obtain the association information on the food. The information on the total calories of the food may be obtained on the basis of depth information on the food obtained through the camera and nutritional information on each of the food obtained from an external electronic device (e.g., a server) or the memory in response to the identification.

Figure 14:
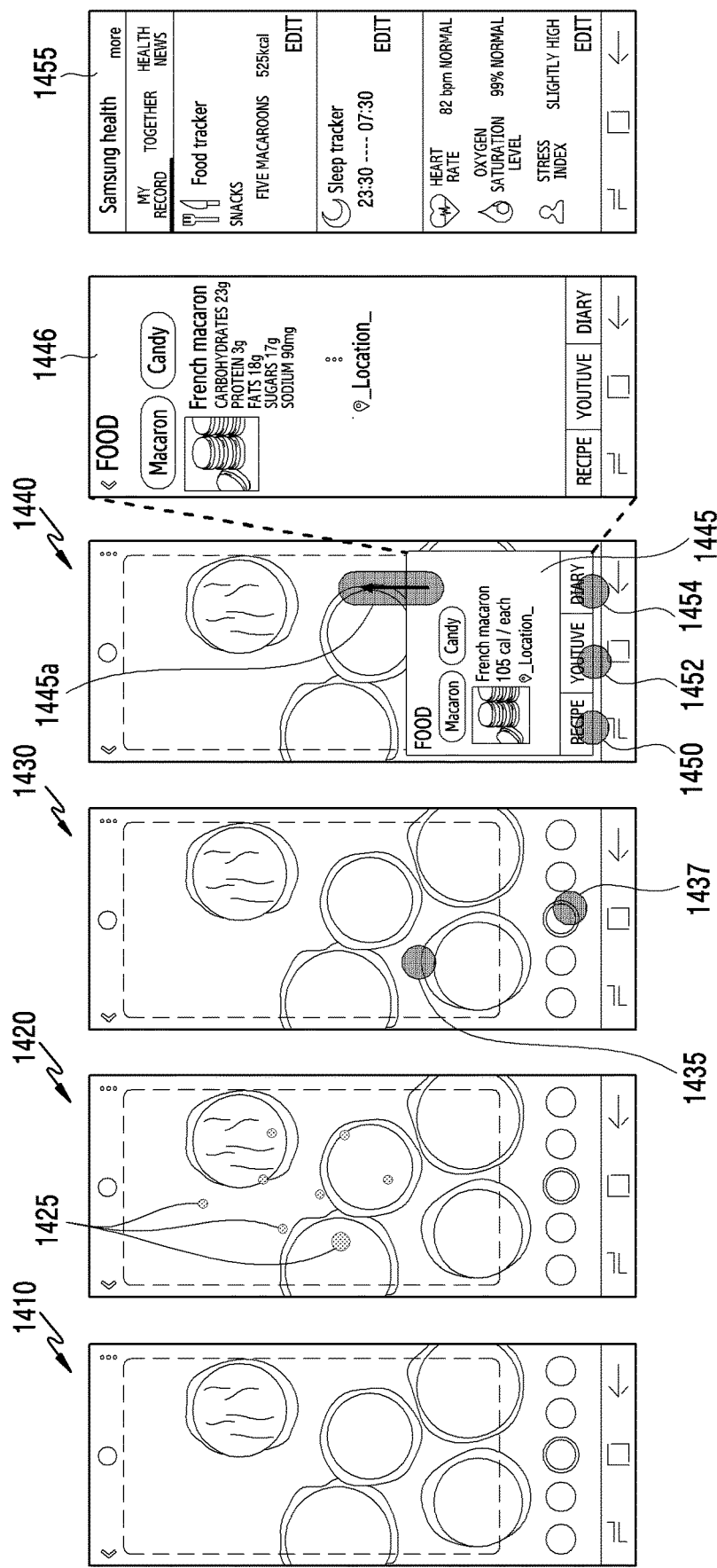
FIG. 14 illustrates an example of a user interface displayed on an electronic device according to various embodiments.

For example, referring to FIG. 14, the processor 120 may display an image that includes objects associated with food and is obtained by at least one camera via a user interface 1410 of the application providing the image recognition service. The processor 120 starts to analyze the image when it is detected that the view (FOV or AOV) of at least one camera of the electronic device 101 is maintained for a specified time or that the image obtained via the at least one camera remains unchanged for the specified time. For example, the processor 120 may extract at least one feature in the image and may extract characteristics (e.g., texture, surface, and curvature) of a plurality of objects in the image, thereby identifying that the objects correspond to the main subject. The processor 120 may retrieve the database of the electronic device 101 or may retrieve a database of at least one external electronic device (e.g., a web server, and an artificial intelligence service server) associated with the electronic device 101 using the information on the objects on the basis of the identification, thereby identifying that the objects are associated with the food. The processor 120 may display an animation effect to indicate that an object in the image is being recognized while performing the identification. For example, the processor 120 may display a user interface 1420 changed from the user interface 1410. In various embodiments, compared to the user interface 1410, the user interface 1420 may display an animation effect 1425 to indicate that the objects (e.g., macaroons) in the image are in the process of being recognized.

The processor 120 may perform operation 1310 and operation 1320 on the basis of identifying that the objects are associated with the food, thereby displaying the icon associated with the second information in a user interface 1430 changed from the user interface 1420. In various embodiments, the icon associated with the second information may be configured with a transparent layer superimposed on the image. In various embodiments, the icon associated with the second information may include data (e.g., the types of the food, for example, macaroons), classifications of the food (e.g. dessert), and the total calories of each of the food (e.g., 105 cal/each), which are included in the second information.

The processor 120 may display a user interface 1440 changed from the user interface 1430 when detecting an input 1437 selecting a shooting button within the user interface 1430. The user interface 1440 may display the captured image—e.g., apparently as a fixed view or a frozen view. In various embodiments, the images displayed in the user interface 1410, the user interface 1420, and the user interface 1430 prior to capture are images (e.g., preview images) corresponding to a live view, while the image displayed in the user interface 1440 after capture may be an image corresponding to a fixed view.

The processor 120 may display at least some of association information 1445 in the user interface 1440 changed from the user interface 1430 when detecting an input 1435 for the icon associated with the second information in the user interface 1430. The association information 1445 displayed in the user interface 1440 in FIG. 14 shows an example in which the input 1435 is detected after the input 1437 is detected, which is for the convenience of explanation. When the input 1435 for the icon associated with the second information is detected in the user interface 1430, the processor 120 may display the association information 1445 superimposed on the image corresponding to the live view.

The processor 120 may receive various inputs while displaying the association information 1445 in the user interface 1440.

For example, the processor 120 may receive an input 1445a for dragging the association information 1445 in a first direction (upward direction in FIG. 14). The processor 120 may display association information 1446 superimposed on the user interface 1440 in response to the received input 1445a. The association information 1446 may be an extension of the association information 1445. For example, the association information 1446 may be detailed information of the association information 1445.

In another example, when an input 1450 for a first icon of at least one icon in the association information 1445 is received, the processor 120 may access a website providing a recipe associated with each of the objects.

In still another example, when an input 1452 for a second icon of the at least one icon in the association information 1445 is received, the processor 120 may access a website (e.g., a Social Networking Service "SNS" website) for uploading the image or a website providing a method for cooking food associated with the image.

In yet another example, when an input 1454 for a third icon of the at least one icon in the association information 1445 is received, the processor 120 may execute another application (e.g., a healthcare service application) associated with food and the application (e.g., the application providing the image recognition service). When the other application is executed, the processor 120 may display a user interface 1455 of the other application changed from the user interface 1440. The user interface 1455 may include not only biometric information on a user but also at least some of the information (e.g., the association information, the second information, and the image) included in the user interface 1440. In various embodiments, the processor 120 may insert (include) information obtained through the application in the user interface of the other application or a memory region allocated for the other application through connection between the application and the other application.

Figure 15:
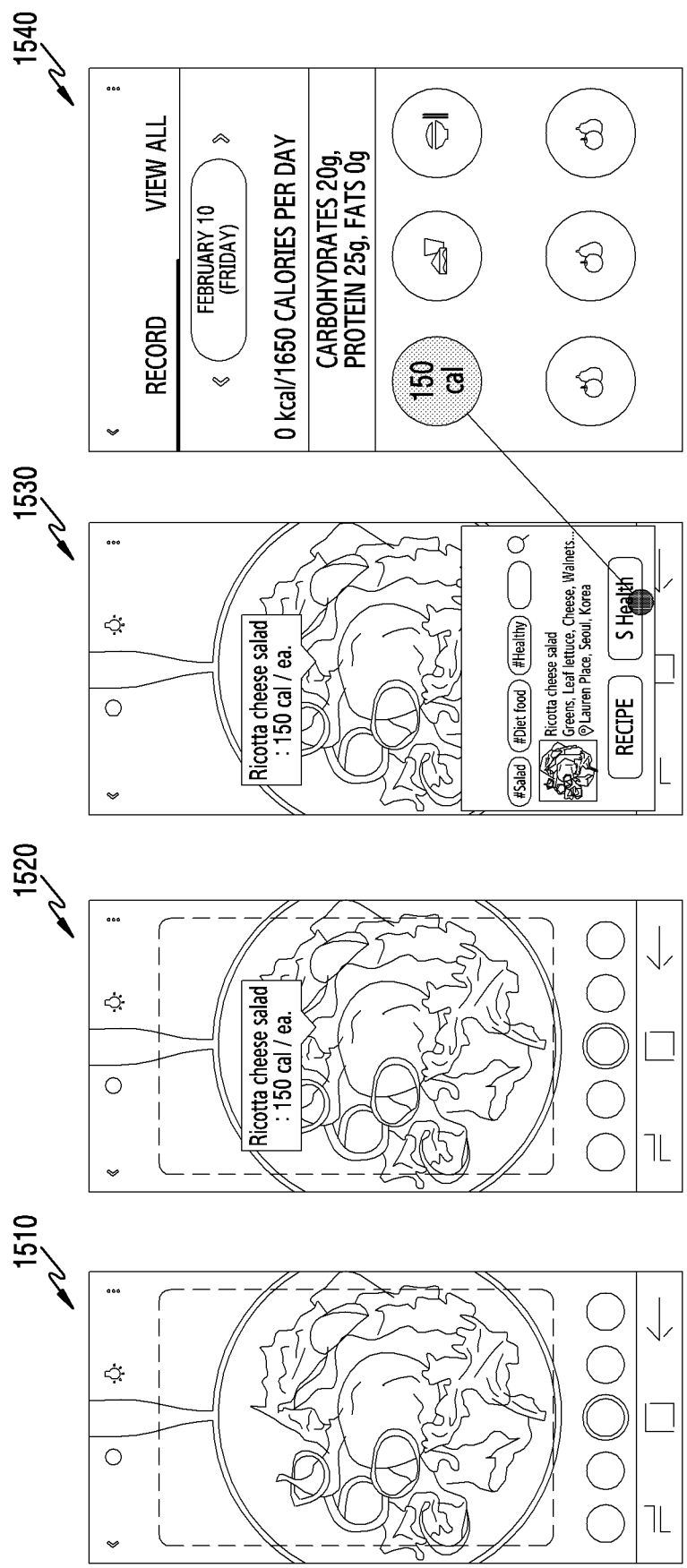
FIG. 15 illustrates another example of a user interface displayed on an electronic device according to various embodiments.

In another example, referring to FIG. 15, the processor 120 may display an image that includes objects associated with food and is obtained by at least one camera via a user interface 1510 of the application providing the image recognition service. When the objects included in the image are recognized, the processor 120 may display a user interface 1520 changed from the user interface 1510. In various embodiments, the user interface 1520 may display information on the food (e.g., ricotta cheese salad) associated with the respective objects and information on the total calories (e.g., 150 cal/ea) of each of the food. The information on the food and the information on the total calories may be superimposed on the image. When an input for a menu icon in the user interface 1520 is detected, the processor 120 may display a user interface 1530 changed from the user interface 1520. The user interface 1530 may include association information on the food. The association information may be superimposed on the image. The association information may include at least one icon associated with the association information. When detecting an input for an icon for accessing the other application linked with the application among the at least one icon included in the association information, the processor 120 may display a user interface 1540 changed from the user interface 1530. The user interface 1540 may correspond to an execution screen of the other application different from the application. The user interface 1540 may include detailed information on the food (e.g., ricotta cheese salad). For example, the detailed information may include at least one of amount information on nutrients of the food, calorie information on the food, and information on the time when the image is obtained. For example, when the image is obtained in a time period associated with breakfast, the processor 120 may insert information on the calories of the food in a breakfast section in the user interface 1540. In various embodiments, to bypass, jump, or skip directly inputting information on the calories of food eaten by a user to the other application providing the healthcare service, the processor 120 may allocate and store the information on the calories of the food by time through an input for the at least one icon included in the association information in the user interface 1530. For example, to bypass inputting the calories of intake through a touch input, the processor 120 may convert the recommended intake of food identified by voice recognition among the plurality of food into a target intake. In another example, to bypass inputting the calories of intake through voice recognition, the processor 120 may display guide information giving an instruction to obtain an image corresponding to a second time after intake. The processor 120 may identify food, the volume (of length) of which is reduced among the plurality of food, on the basis of the image at the second time obtained in response to the display. The processor 120 may obtain information on the calories of food eaten by the user on the basis of the identified food and a change in the volume of the identified food.

As described above, the electronic device 101 according to various embodiments may connect the application providing the image recognition service with the application providing the healthcare service, thereby easily managing the user's health information related to the intake of food. With this management, the electronic device 101 according to various embodiments may provide enhanced user experience (UX).

Figure 16:
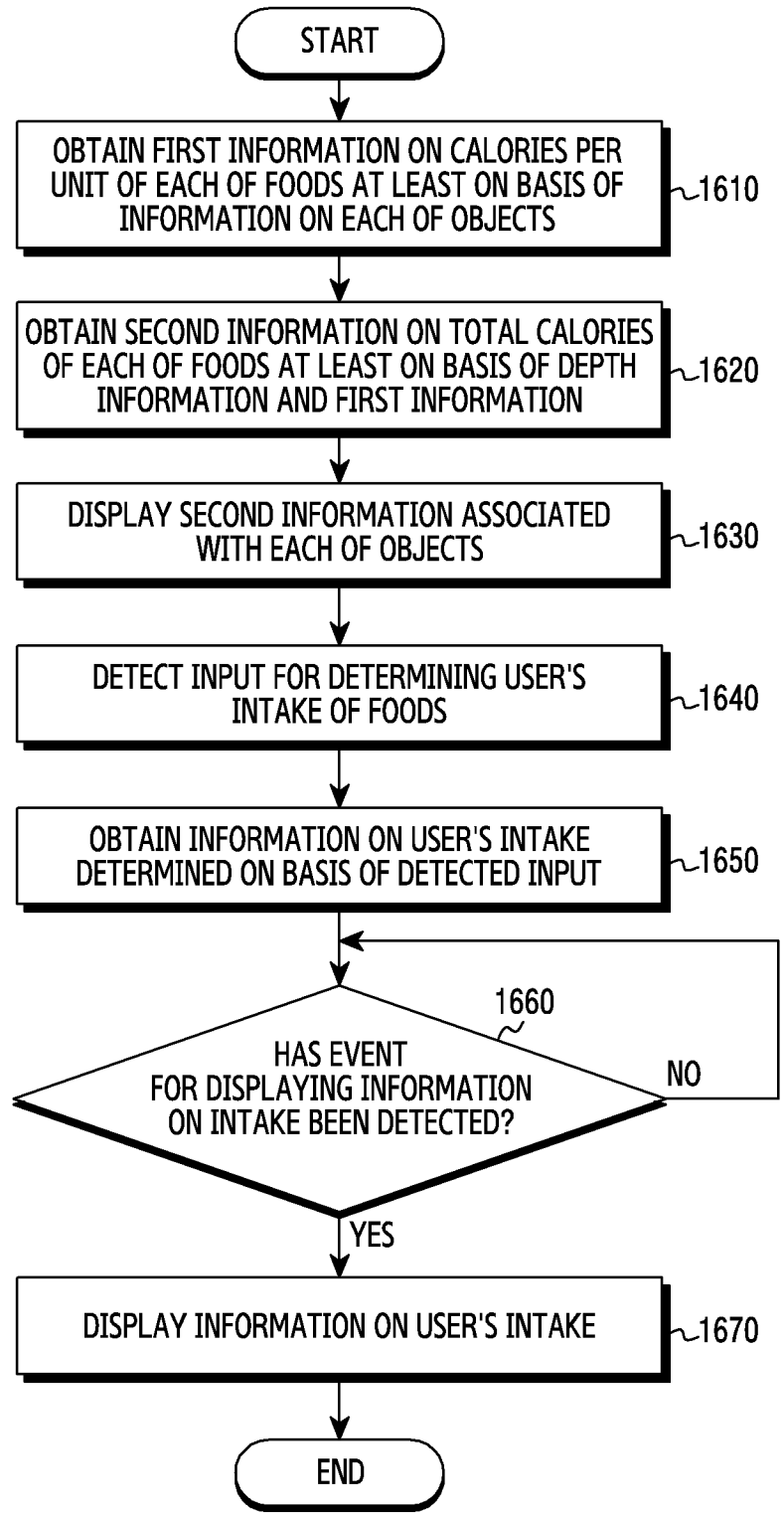
FIG. 16 illustrates an example of the operation of an electronic device obtaining intake information according to various embodiments.

FIG. 16 illustrates an example of the operation of an electronic device obtaining intake information according to various embodiments. This operation may be performed by the electronic device 101 shown in FIG. 1, the electronic device 101 shown in FIG. 2, the processor 120 of the electronic device 101 shown in FIG. 1, or the processor 120 of the electronic device 101 shown in FIG. 2.

Operations 1610 to 1670 in FIG. 16 may be associated with operation 440 in FIG. 4.

Referring to FIG. 16, in operation 1610, the processor 120 may obtain first information on calories per unit of each of food at least on the basis of information on each of objects associated with the food included in an image. In various embodiments, operation 1610 may be the same as or similar to operation 510 in FIG. 5.

In operation 1620, the processor 120 may obtain second information on the total calories of each of the food at least on the basis of depth information and the first information. In various embodiments, operation 1620 may be the same as or similar to operation 520 in FIG. 5.

In operation 1630, the processor 120 may display the second information associated with each of the objects. In various embodiments, association between each of the objects and the second information may be indicated by displaying the second information superimposed on each of the objects. In various embodiments, the association between each of the objects and the second information may be indicated by a speech balloon (or window) that is directed to each of the objects, overlaps the image, and includes the second information.

Figure 17:
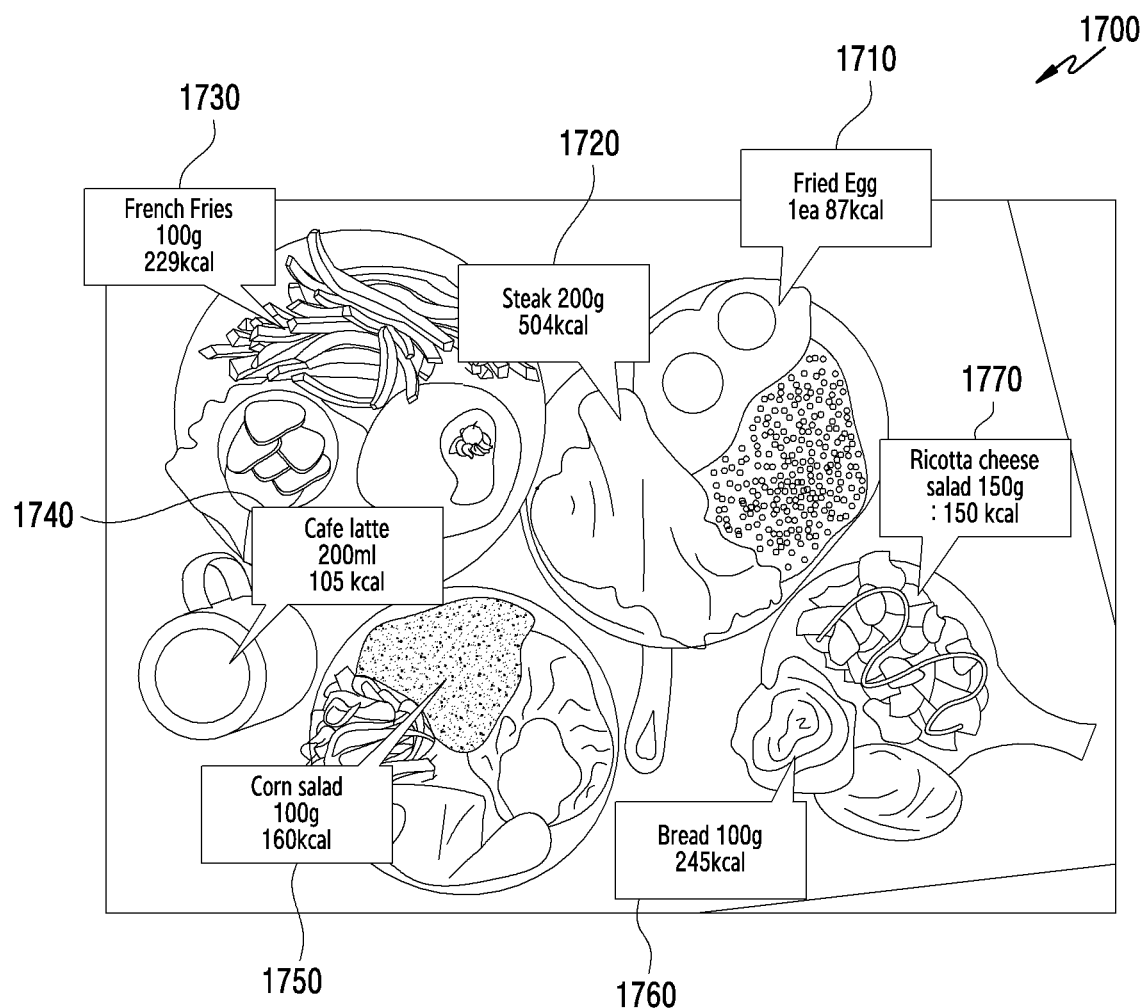
FIG. 17 illustrates yet another example of an image displayed on an electronic device according to various embodiments.

For example, referring to FIG. 17, the processor 120 may display an image 1700 including the objects associated with the food. The image 1700 may include second information 1710 that is associated with an object related to a fried egg and indicates the total calories of a fried egg (87 kcal/ea), second information 1720 that is associated with an object related to a steak and indicates the total calories of a steak (504 kcal/200 g), second information 1730 that is associated with an object related to French fries and indicates the total calories of French fries (229 kcal/100 g), second information 1740 that is associated with an object related to a cafe latte and indicates the total calories of a cafe latte (105 kcal/200 ml), second information 1750 that is associated with an object related to a corn salad and indicates the total calories of a corn salad (160 kcal/100 g), second information 1760 that is associated with an object related to bread and indicates the total calories of bread (245 kcal/100 g), and second information 1770 that is associated with an object related to a ricotta cheese salad and indicates the total calories of a ricotta cheese salad (150 kcal/150 g). The user may recognize the total calories of each of the food associated with the objects included in the image 1700 through the image 1700.

Figure 18:
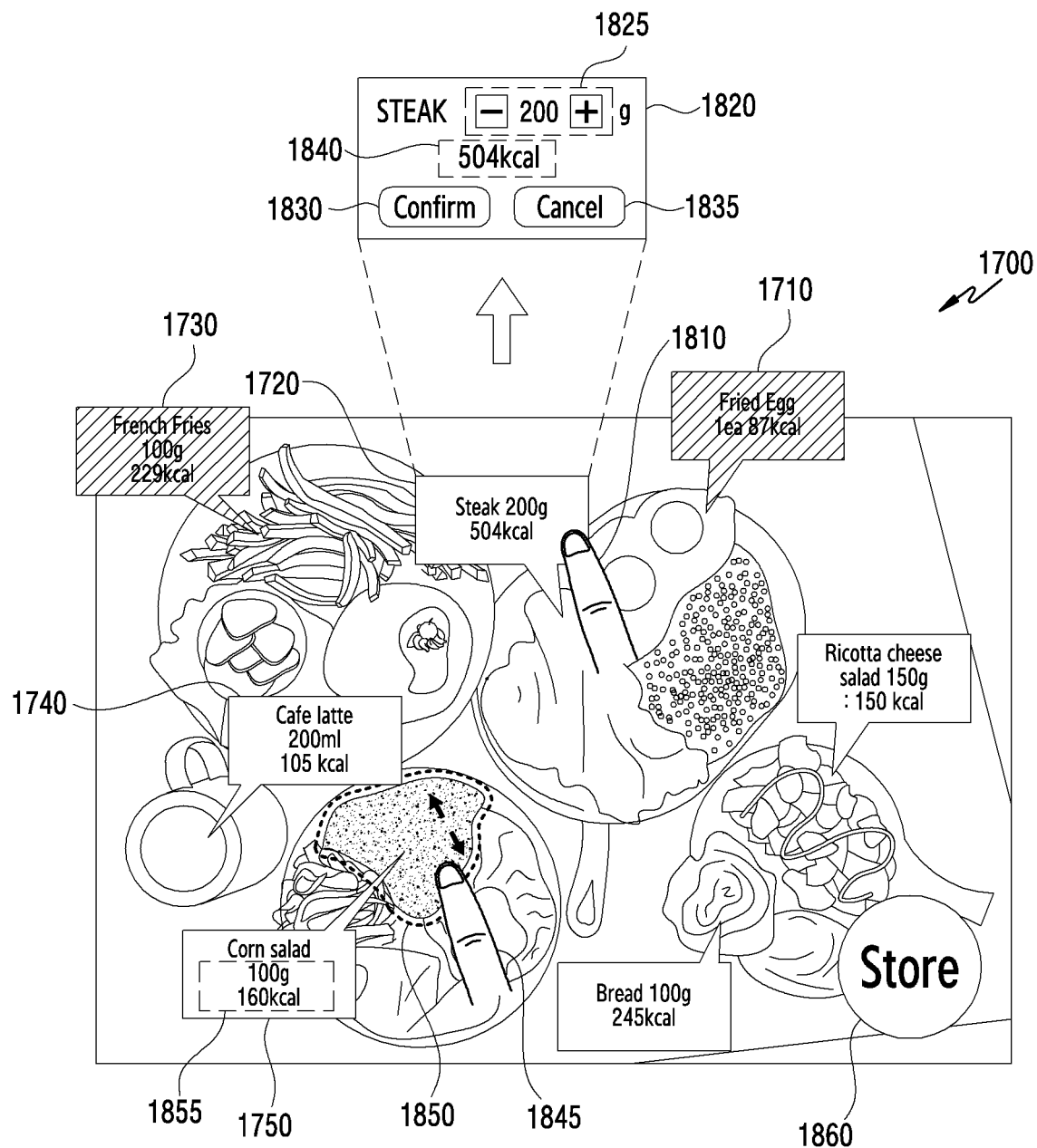
FIG. 18 illustrates still another example of an image displayed on an electronic device according to various embodiments.

In operation 1640, the processor 120 may detect an input for determining the user's intake of the food. In various embodiments, the input may be entered via the second information displayed in the image. In various embodiments, the input may be entered via an object displayed in the image. In various embodiments, the input may be entered after the user eats the food associated with the objects included in the image or before the user eats the food associated with the objects included in the image. In various embodiments, the input may include receiving information on an image obtained by an external electronic device (e.g., a wearable device, such as smart glasses, or an Internet of Things (IoT) device) associated with the electronic device 101 from the external electronic device. In various embodiments, the external electronic device may refer to a device that is capable of photographing the food associated with the user while the user is eating. FIG. 18 will show an example in which the user causes the input before eating the food, which is for the convenience of explanation.

For example, referring to FIG. 18, the processor 120 may detect an input 1810 for the second information 1720 in the image 1700. The processor 120 may display a window 1820 changed from the second information 1720 in response to the detected input 1810. In various embodiments, the window 1820 may include elements for determining the user's intake (or estimated intake) of the steak. In various embodiments, the window 1820 may include an executable object 1825 for inputting the user's intake (or estimated intake). In various embodiments, the window 1820 may further include an executable object 1830 for fixing a value entered via the object 1825. In various embodiments, the window 1820 may further include an executable object 1835 for canceling a value entered via the object 1825.

In various embodiments, the window 1820 may further include an object 1840 that displays the user's intake (or estimated intake) calculated according to a value input via the object 1825.

In another example, referring to FIG. 18, the processor 120 may detect an input for the object associated with the corn salad in the image 1700. In various embodiments, the input may include a single-tap input, a double-tap input, a drag input, a force-touch input, a long-press input, or a hovering input. In various embodiments, when the input is detected, the processor 120 may display a region 1850 for determining the user's intake (or estimated intake). In various embodiments, the processor 120 may detect an input 1845 for the region 1850. The input 1845 may include a drag input for changing the area of the region 1850. The processor 120 may identify the user's intake of a corn salad on the basis of the input 1845. For example, the processor 120 may identify the user's intake on the basis of the area of the region 1850 changed by the input 1845. In various embodiments, the processor 120 may indicate the identified user's intake by changing an indicator 1855 (e.g., 160 kcal/100 g) in the second information 1750.

In various embodiments, the processor 120 may display an object 1860 for storing the user's intake in the memory 130. In various embodiments, the object 1860 may be displayed on the basis of an input for the image (e.g., the image 1700). In various embodiments, an attribute of the input for the image 1700 may be distinct from an attribute of the input (e.g., the input 1810) for the second information. In various embodiments, the attribute of the input for the image 1700 may be distinct from an attribute of the input (e.g., the input 1845) for the object. In various embodiments, the object 1860 may be displayed in the image 1700 when receiving an input, such as the input 1810 and the input 1845.

In operation 1650, the processor 120 may obtain information on the user's intake determined on the basis of the detected input. In various embodiments, the processor 120 may obtain the information on the user's intake on the basis of a value specified by the detected input. For example, referring to FIG. 18, when detecting an input for the object 1860, the processor 120 may obtain information on the user's intake on the basis of the second information currently provided in the image 1700 and may store the obtained information in the memory 130. In various embodiments, the obtained information may be linked with or provided to an application providing a healthcare service.

In operation 1660, the processor 120 may detect whether an event for displaying the information on the intake occurs. In various embodiments, the event may include executing an application providing a healthcare service. In various embodiments, the event may include detecting that the determined user's intake is fixed, such as detecting the input for the object 1860. In various embodiments, the event may include the approach of a time period for which a user receives a service related to food intake. However, the present disclosure is not limited thereto.

In operation 1670, the processor 120 may display the information on the user's intake when detecting that the event has occurred. In various embodiments, the processor 120 may display the information on the user's intake in a user interface of the application providing the healthcare service.

Figure 19:
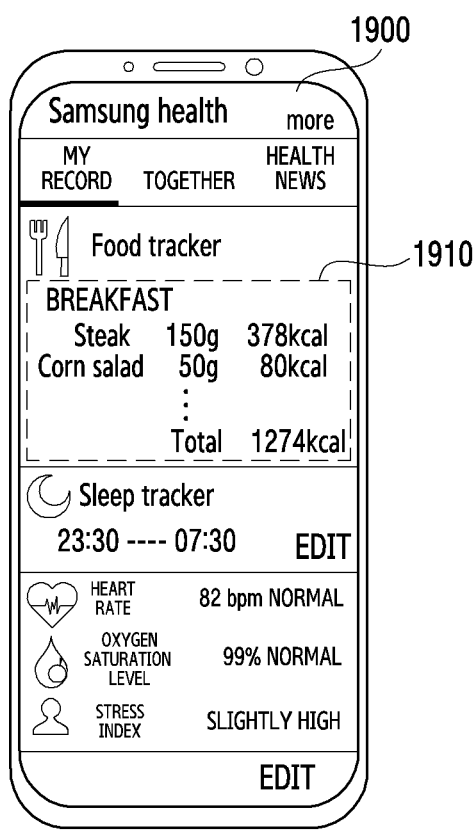
FIG. 19 illustrates still another example of a user interface displayed on an electronic device according to various embodiments.

For example, referring to FIG. 19, the processor 120 may display information 1910 on the user's intake in a user interface 1900 of the application. The information 1910 may include at least one of information on a time period in which the user ate food, information on the type of the food that the user ate in the time period, information on the intake of the food, and information on the user's total intake in the time period. In various embodiments, the information 1910 may be displayed in the user interface 1900 along with other information (e.g., sleeping information on the user, heart rate information on the user, oxygen saturation information on the user, and stress information on the user).

As described above, the electronic device 101 according to various embodiments may provide a user interface which enables the user to determine an intake through an image of food, thereby bypassing an operation in which the user directly inputs an intake via a user interface of a healthcare application. Due to this bypassing, the electronic device 101 can provide an enhanced user experience.

Figure 20:
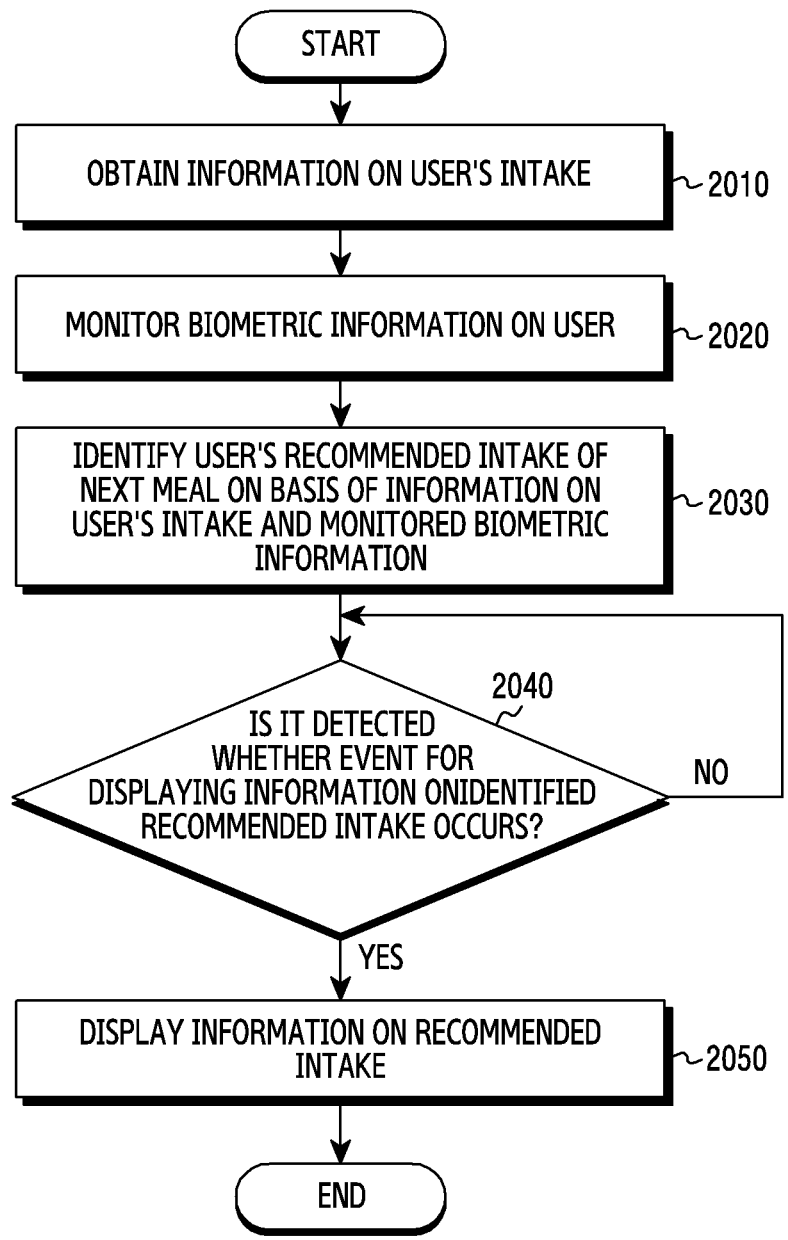
FIG. 20 illustrates an example of the operation of an electronic device displaying information on a recommended intake according to various embodiments.
Figure 21:
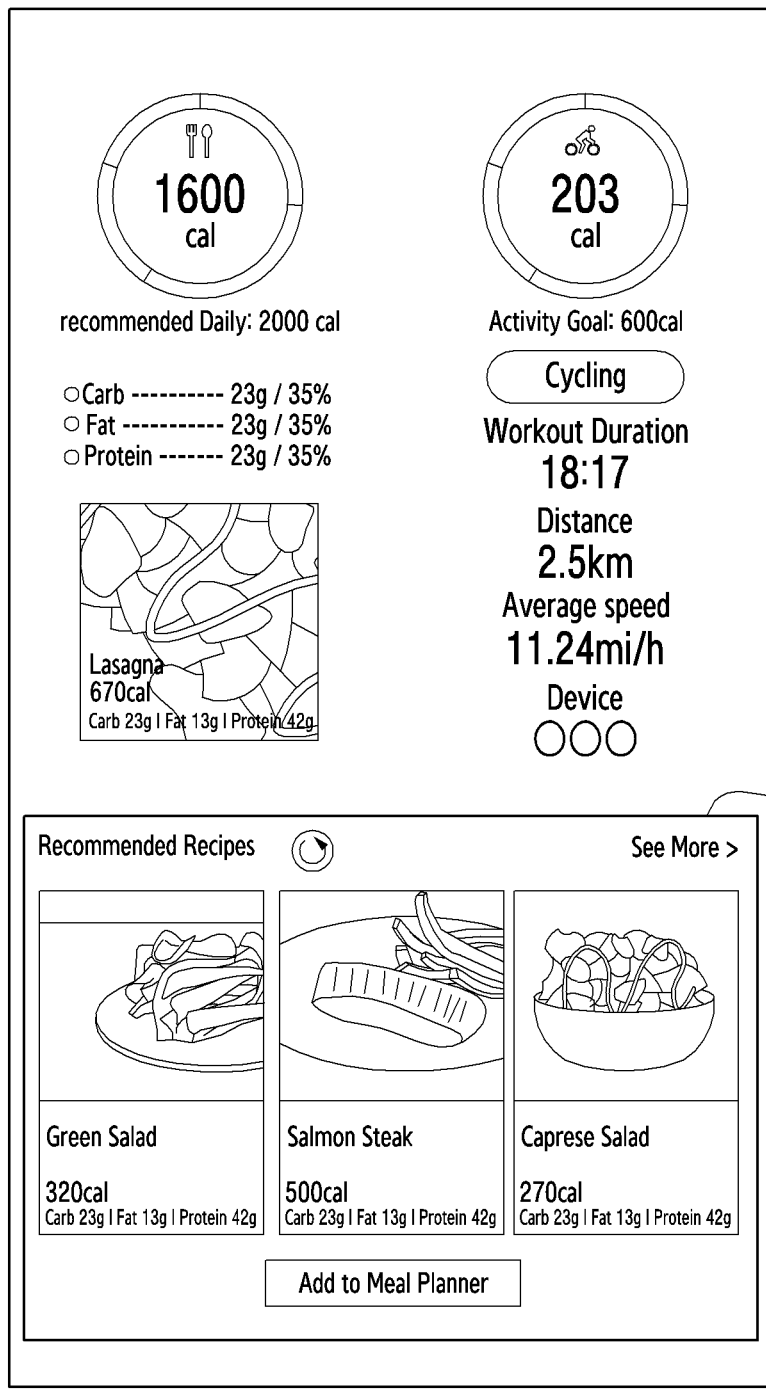
FIG. 21 illustrates yet another example of a user interface displayed on an electronic device according to various embodiments.

FIG. 20 illustrates an example of the operation of an electronic device displaying information on a recommended intake according to various embodiments. This operation may be performed by the electronic device 101 shown in FIG. 1, the electronic device 101 shown in FIG. 2, the processor 120 of the electronic device 101 shown in FIG. 1, or the processor 120 of the electronic device 101 shown in FIG. 2.

Referring to FIG. 20, in operation 2010, the processor 120 may obtain information on a user's intake. Operation 2010 may be the same as or similar to operation 1650.

In operation 2020, the processor 120 may monitor biometric information on the user. In various embodiments, the processor 120 may monitor the biometric information on the user that is changed after obtaining the information on the user's intake.

In operation 2030, the processor 120 may identify the user's recommended intake of a next meal on the basis of the information on the user's intake and the monitored biometric information.

In operation 2040, the processor 120 may detect whether an event for displaying information on the identified recommended intake occurs. In various embodiments, the event may include executing an application providing a healthcare service. In various embodiments, the event may include the approach of a specified time period (e.g., next meal time). However, the present disclosure is not limited thereto. In various embodiments, the information on the recommended intake may include data on the recommended intake of the next meal. In various embodiments, the information on the recommended intake may include data on the type of food corresponding to (or matching) the recommended intake of the next meal. In various embodiments, the information on the recommended intake may include data on a recipe of food corresponding to the recommended intake of the next meal.

In operation 2050, the processor 120 may display the information on the recommended intake when detecting that the event for displaying the information on the recommended intake has occurred. For example, referring to FIG. 21, upon the detection, the processor 120 may display a user interface 2100 of an application providing a healthcare service. In various embodiments, the user interface 2100 may include information 2110 including thumbnail images to access recipes of the food corresponding to the recommended intake of the next meal. When detecting an input for one of the thumbnail images (e.g., a thumbnail image associated with a green salad, a thumbnail image associated with a salmon salad, and a thumbnail image associated with a 'Caprese' salad) included in the information 2110, the processor 120 may display a recipe of food represented by the one thumbnail image.

In various embodiments, the information 2110 may be displayed in the user interface 2100 along with other information. For example, the information 2110 may be displayed along with information on the user's previous meal. In another example, the information 2110 may be displayed along with calorie consumption information (or exercise history information) on the user.

In various embodiments, the information 2110 may be displayed in an external electronic device linked to the electronic device 101. For example, the processor 120 may transmit biometric information on the user and information on the user's food intake, which are obtained by the healthcare application, to a server (e.g., a server for an IoT hub). The server may obtain the information 2110 at least on the basis of the biometric information and the information on the food intake. The server may transmit the obtained information 2110 to the external electronic device (e.g., a refrigerator with a display) that is distinguished from the electronic device 101 and is linked to the electronic device 101. The external electronic device may display the information 2110 through a display of the other electronic device. In various embodiments, when the external electronic device is a refrigerator with a display, the external electronic device may further display, along with the information 2110, guide information for purchasing at least one ingredient, other than an ingredient included in the refrigerator, among ingredients utilized to make the food corresponding to the recommended intake of the next meal. For example, when ingredient A and ingredient B for preparing the next meal are stored in the refrigerator but ingredient C is not stored, the external electronic device may display, along with the information 2110, information on a place (e.g., a website) selling ingredient C, price information on ingredient C, or discount information on ingredient C in order to guide the user on the purchase of ingredient C. However, the present disclosure is not limited thereto.

As discussed above, the electronic device 101 according to various embodiments may display information on the recommended intake of the next meal so that the user can improve eating habits.

Figure 22:
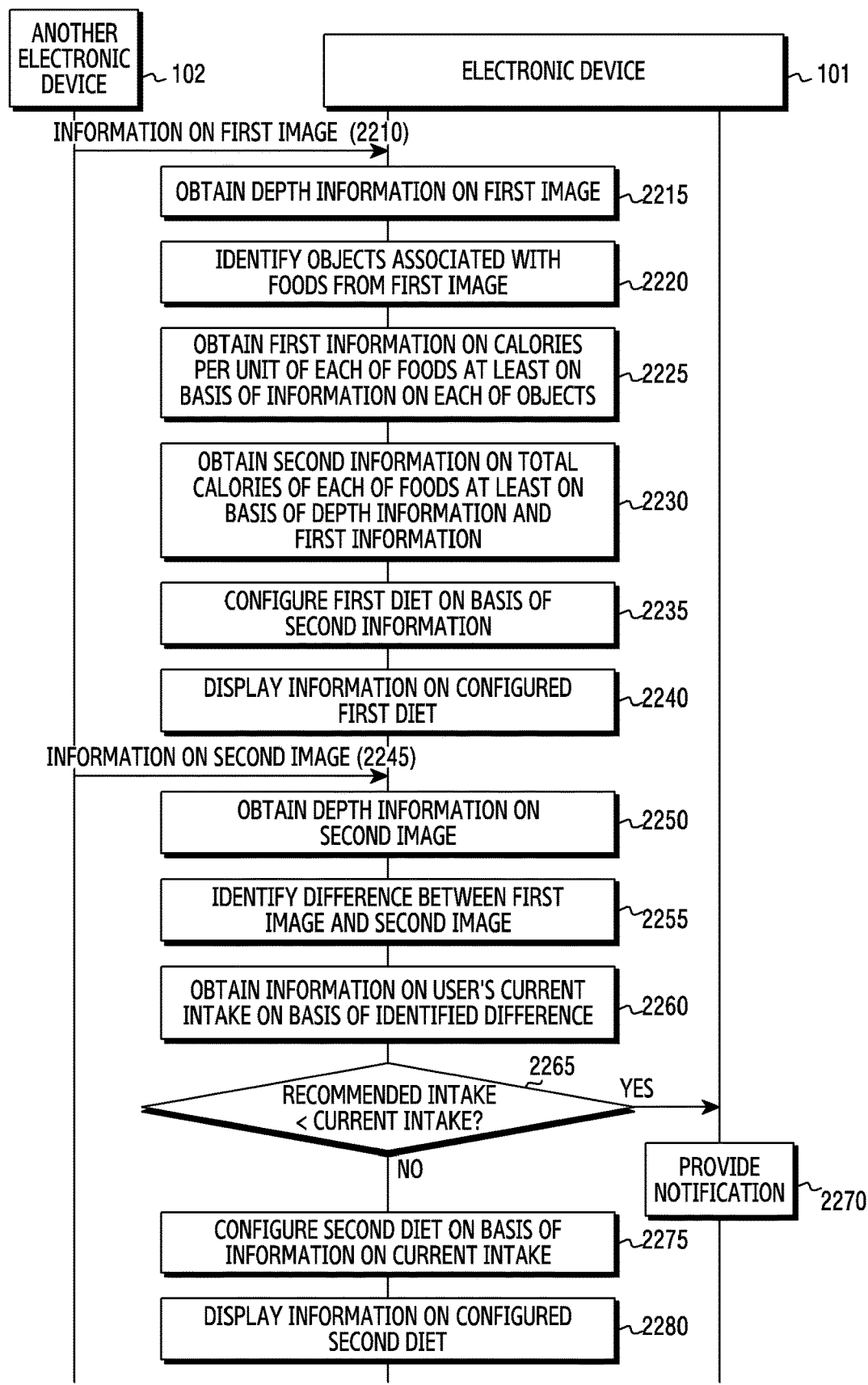
FIG. 22 illustrates an example of linkage between an electronic device and another electronic device according to various embodiments.

FIG. 22 illustrates an example of linkage between an electronic device and another electronic device according to various embodiments. This linkage may occur between the electronic device 101 shown in FIG. 1 or FIG. 2 and the electronic device 102 shown in FIG. 1.

Referring to FIG. 22, in operation 2210, the other electronic device 102 may transmit information on a first image to the electronic device 101. In various embodiments, the other electronic device 102 may include at least one camera for obtaining an image. In various embodiments, the other electronic device 102 may be a device linked with the electronic device 101. For example, the other electronic device 102 may include a wearable device (e.g., smart glasses) linked with the electronic device 101. Alternatively, the other electronic device 102 may include an IoT device (e.g., a smart bulb with a camera and a camera installed on a ceiling) that is linked with the electronic device 101) and is installed on a table or the like. However, the present disclosure is not limited thereto.

In various embodiments, the first image may include objects associated with food. In various embodiments, when it is identified that a certain subject enters the view of the at least one camera of the other electronic device 102, the other electronic device 102 may transmit the information on the first image to the electronic device 101. In various embodiments, when it is identified that a connection between the other electronic device 102 and the electronic device 101 is established, the other electronic device 102 transmit the information on the first image to the electronic device 101. In various embodiments, when it is identified that a designated time period has come, the other electronic device 102 transmit the information on the first image to the electronic device 101. However, the present disclosure is not limited thereto. The electronic device 101 may receive the information on the first image from the other electronic device 102.

In operation 2215, the electronic device 101 may obtain depth information on the first image. In various embodiments, the depth information may be included in the information on the first image. In various embodiments, the depth information may be obtained through image processing of the first image by the electronic device 101. However, the present disclosure is not limited thereto.

In operation 2220, the electronic device 101 may identify the objects associated with the food from the first image. In various embodiments, the electronic device 101 may identify the objects associated with the food on the basis of processing of the first image by the electronic device 101. In various embodiments, the electronic device 101 may identify the objects associated with the food from the first image through signaling with an external electronic device (e.g., an artificial intelligence server and an image recognition server) distinguished from the electronic device 101 and the other electronic devices 102.

In operation 2225, the electronic device 101 may obtain first information on calories per unit of each of the food at least on the basis of information on each of the objects. In various embodiments, the electronic device 101 may obtain the first information using a database stored in the memory 130 of the electronic device 101. In various embodiments, the electronic device 101 may obtain the first information through signaling with an external electronic device (e.g., a server of a particular webpage or a server that provides a food-related service) linked with the electronic device 101.

In operation 2230, the electronic device 101 may obtain second information on the total calories of each of the food at least on the basis of the depth information and the first information. In various embodiments, the electronic device 101 may identify the amount of each of the food through the depth information and may obtain the second information using information on the identified amount and the first information.

In operation 2235, the electronic device 101 may configure a first diet on the basis of the second information. In various embodiments, the first diet may be configured on the basis of a recommended intake for a user associated with the electronic device 101 that is identified at least on the basis of the second information.

In operation 2240, the electronic device 101 may display information on the configured first diet. For example, the electronic device 101 may display the information on the first diet as illustrated in the example of FIG. 8.

In operation 2245, the other electronic device 102 may transmit information on a second image to the electronic device 101. In various embodiments, the second image may include the objects associated with the food that have been changed (or reduced) by the user's intake after displaying the information on the first diet.

The interval between the transmission of the first image and the transmission of the second image may be set variously. For example, the other electronic device 102 may transmit an image (e.g., second image) related to (or changed from) the first image at a specified interval after transmitting the first image. Alternatively, when it is identified that the difference between the first image and an image obtained after transmitting the first image is greater than a reference level, the other electronic device 102 may transmit the image (e.g., second image) obtained after transmitting the first image. However, the present disclosure is not limited thereto.

The electronic device 101 may receive the information on the second image from the other electronic device 102.

In operation 2250, the electronic device 101 may obtain depth information on the second image. In various embodiments, the depth information may be used to identify the difference between the amount of each of the food associated with the objects included in the first image and the amount of each of the food associated with the objects included in the second image.

In operation 2255, the electronic device 101 may identify a difference between the first image and the second image. In various embodiments, the electronic device 101 may identify the difference between the first image and the second image in order to recognize the user's intake at the current meal. Operation 2255 shows an example of identifying the difference between the first image and the second image but may be replaced with at least one other operation.

For example, operation 2255 may be replaced with operations 2220 through 2230. However, the present disclosure is not limited thereto.

In operation 2260, the electronic device 101 may obtain information on the user's current intake on the basis of the identified difference. For example, the electronic device 101 may obtain information on the user's current intake on the basis of the difference between the depth information on the first image and the depth information on the second image.

In operation 2265, the electronic device 101 may identify whether the identified current intake is greater than the recommended intake for the user. In various embodiments, when the current intake is greater than the recommended intake, the electronic device 101 may perform operation 2270. In various embodiments, when the current intake is less than the recommended intake, the electronic device 101 may perform operation 2275.

In operation 2270, when it is identified that the current intake is greater than the recommended intake, the electronic device 101 may provide a notification. In various embodiments, the notification may be used to indicate that the user is currently overeating food. In various embodiments, the notification may be provided by displaying a screen, by outputting a voice, or by changing the color of a light-emitting diode functioning as an indicator. However, the present disclosure is not limited thereto.

In operation 2275, the electronic device 101 may configure a second diet on the basis of information on the current intake. In various embodiments, the electronic device 101 may recognize the type of food eaten by the user and the ratio of nutrients eaten by the user on the basis of the information on the current intake. The electronic device 101 may configure the second diet changed from the first diet on the basis of the recognition.

In operation 2280, the electronic device 101 may display information on the configured second diet. In various embodiments, the information on the second diet may be information representing a context changed depending on the user's intake.

As described above, the electronic device 101 according to various embodiments may change a diet adequate for the user in real time via link with the other electronic device 102 capable of photographing the user eating food in real time. The electronic device 101 according to various embodiments may provide a diet that can improve the user's health in accordance with the user's eating situation through the change.

As described above, an electronic device (e.g., the electronic device 101) according to various embodiments may include: a memory (e.g., the memory 130) configured to store instructions; at least one camera (e.g., the camera module 180); at least one display (e.g., the display device 160); and at least one processor (e.g., the processor 120), wherein the at least one processor may be configured to: obtain an image using the at least one camera; identify a plurality of objects associated with a plurality of food from the image; obtain information on a recommended intake associated with the plurality of identified objects; display the image; and execute the stored instructions to display a plurality of indications for indicating the recommended intake in association with the plurality of objects included in the image.

According to various embodiments, each of the indications may be superimposed on each of the plurality of objects.

According to various embodiments, each of the indications may be displayed by highlighting a region corresponding to the recommended intake within a region occupied by each of the plurality of objects.

According to various embodiments, the at least one processor may be further configured to: detect an input for changing a recommended intake of each of at least one food associated with at least one object among the plurality of objects to a target intake; and execute the stored instructions to change a display of at least some of the plurality of indications at least on the basis of a change to the target intake of each of the at least one food. For example, the at least one processor may be configured to: change the recommended intake of each of the at least one food into the target intake on the basis of the detected input; identify a recommended intake of each of remaining food at least on the basis of the changed target intake; and execute the stored instructions to change a display of at least one indication associated with the at least one object and indications associated with at least some of the remaining food at least on the basis of the target intake of each of the at least one food and the recommended intake of each of the remaining food. For example, the input may be a drag input for enlarging or reducing at least one indication associated with the at least one object among the plurality of indications.

According to various embodiments, the at least one processor may be further configured to: obtain depth information on the image; obtain first information on calories per unit of each of the plurality of food at least on the basis of the depth information; obtain second information on total calories of each of the plurality of food at least on the basis of the depth information and the first information; and execute the stored instructions to obtain information on a recommended intake of each of the plurality of food at least one the basis of the second information.

According to various embodiments, the at least one processor may be configured to execute the stored instructions to obtain information on a recommended intake of each of the plurality of food on the basis of the information on the recommended intake and information on a food intake history of a user associated with the electronic device.

According to various embodiments, the electronic device may further include a communication interface (e.g., the communication module 190), wherein the at least one processor may be further configured to: execute the stored instructions to receive information on a calorie consumption of a user associated with the electronic device through the communication interface; and execute the stored instructions to obtain information on a recommended intake of each of the plurality of food at least on the basis of the information on the calorie consumption and the second information.

According to various embodiments, the at least one processor may be further configured to: obtain abstract information on at least one food among the plurality of food at least on the basis of information on each of the plurality of objects associated with the plurality of food from the image; display the abstract information that is superimposed on the image obtained through the at least one camera; and execute the stored instructions to display detailed information on the at least one food changed from the abstract information in response to detection of an input for the abstract information. For example, the electronic device may further include a communication interface, wherein the detailed information may include at least one icon for accessing at least one website, and the at least one processor may be further configured to execute the stored instructions to access a website indicated by an icon through the communication interface in response to detection of an input for the icon among the at least one icon.

As described above, an electronic device according to various embodiments may include: a memory configured to store instructions; at least one camera; at least one display; and at least one processor, wherein the at least one processor may be configured to: display indications for indicating a recommended intake of each of food along with an image that is obtained through the at least one camera and includes objects associated with the food; detect a user input for changing a recommended intake of food associated with a first indication among the food to a target intake; and execute the stored instructions to change a size of the first indication among the indications and to change a size of a second indication, distinct from the first indication, among the indications on the basis of the user input.

According to various embodiments, the size of the first indication may be changed to indicate the target intake of the food, and the size of the second indication may be changed to indicate a recommended intake of another food changed on the basis of the target intake. For example, the at least one processor may be further configured to execute the stored instructions to cease displaying a third indication, distinct from the first indication and the second indication, among the indications on the basis of the user input.

According to various embodiments, each of the indications may be displayed by highlighting a region corresponding to the recommended intake within a region occupied by each of the objects. For example, each of the indications may be superimposed on each of the objects. For example, the user input may be a drag input for enlarging or reducing the first indication. For example, the at least one processor may be further configured to execute the stored instructions to display information on total calories of each of the food along with the image and the indications. For example, the information on the total calories may be identified on the basis of depth information on the image.

According to various embodiments, the recommended intake may be obtained on the basis of biometric information on a user associated with the electronic device.

Methods stated in claims and/or specifications according to various embodiments may be implemented by hardware, software, or a combination of hardware and software.

When the methods are implemented by software, a computer-readable storage medium for storing one or more programs (software modules) may be provided. The one or more programs stored in the computer-readable storage medium may be configured for execution by one or more processors within the electronic device. The at least one program may include instructions that cause the electronic device to perform the methods according to various embodiments of the present disclosure as defined by the appended claims and/or disclosed herein.

The programs (software modules or software) may be stored in non-volatile memories including a random access memory and a flash memory, a Read Only Memory (ROM), an Electrically Erasable Programmable Read Only Memory (EEPROM), a magnetic disc storage device, a Compact Disc-ROM (CD-ROM), Digital Versatile Discs (DVDs), or other type optical storage devices, or a magnetic cassette. Alternatively, any combination of some or all of the may form a memory in which the program is stored. Further, a plurality of such memories may be included in the electronic device.

In addition, the programs may be stored in an attachable storage device which is accessible through communication networks such as the Internet, Intranet, local area network (LAN), wide area network (WAN), and storage area network (SAN), or a combination thereof. Such a storage device may access the electronic device via an external port. Further, a separate storage device on the communication network may access a portable electronic device.

In the above-described detailed embodiments of the present disclosure, a component included in the present disclosure is expressed in the singular or the plural according to a presented detailed embodiment. However, the singular form or plural form is selected for convenience of description suitable for the presented situation, and various embodiments of the present disclosure are not limited to a single element or multiple elements thereof. Further, either multiple elements expressed in the description may be configured into a single element or a single element in the description may be configured into multiple elements.

While the present disclosure has been shown and described with reference to certain embodiments thereof, it will be understood by those skilled in the art that various changes in form and details may be made therein without departing from the present disclosure. Therefore, the present disclosure should not be defined as being limited to the embodiments, but should be defined by the appended claims and equivalents thereof.

What is claimed is:

1. An electronic device, comprising:
   at least one camera;
   at least one display;
   at least one processor; and
   a memory storing instructions executable by the at least one processor to cause the electronic device to:
   obtain and display an image using the at least one camera;
   identify a plurality of food items in the image, including a first food item and a second food item;
   obtain nutritional information corresponding to each of the plurality of food items;
   obtain recommendation information including recommended consumption quantities associated with each of the plurality of food items based on the nutritional information, including a first recommended consumption quantity for the first food item and a second recommended consumption quantity for the second food item;
   display a plurality of indications superimposed on the displayed image to represent the recommended consumption quantities for each of the plurality of food items, including a first and second displayed indication respectively superimposed on the first and second food items; and
   in response to detecting an input selecting the first displayed indication, altering a size of the first displayed indication to set a new target consumption quantity for the first food item, and altering a size of a second displayed indication to represent a change in the second recommended consumption quantity for the second food item according to the new target consumption quantity of the first food item, such that a total consumption quantity of the plurality of food items is maintained.

2. The electronic device of claim 1, wherein the input to the first displayed indication altering the size of the first food item includes a multi-touch drag input to the first food item as displayed within the image obtained using the at least one camera, and
   wherein when the size of the first displayed indication is enlarged, the size of the second displayed indication is reduced, to maintain the total consumption quantity of the plurality of food items.

3. The electronic device of claim 2, wherein at least one indication among the plurality of indications includes a highlighting effect imposed over a portion of one food item less than an entirety of the food item, the highlighting effect indicating a recommended consumption quantity of the food item, and
wherein the enlarged size of the first displayed indication and the reduced size of the second displayed indication are displayed simultaneously as superimposed over the displayed image obtained using the at least one camera.

4. The electronic device of claim 1, wherein the plurality of indications comprises a first indication for the first food item and a second indication for the second food item, and
wherein the instructions are further executable by the at least one processor to cause the electronic device to:
change the first indication to correspond to the new target consumption quantity;
calculate new recommended consumption quantity for the second food item based on the new target consumption quantity; and
change the second indication based on the new recommended consumption quantity.

5. The electronic device of claim 1, wherein the instructions are further executable by the at least one processor to cause the electronic device to:
detect an input selecting a first indication for a first food item, and display a window superimposed over at least a portion of the first food item, the window including display objects selectable to change a recommended consumption quantity of the first food item to a new target consumption quantity; and
detect a selection of one of the display objects altering the new target consumption quantity, and in response to the detected input, visually altering the first indication for the first food item to correspond to the altered target consumption quantity.

6. The electronic device of claim 1, wherein depth information is captured when the image is obtained using the at least one camera,
wherein the nutritional information includes calories per unit weight for at least a particular food item in the image, and
wherein the instructions are further executable by the at least one processor to cause the electronic device to:
estimate a weight of the at least the particular food item using the depth information; and
calculate an estimated caloric value of the particular food item based on the estimated weight and the calories per unit weight,
wherein a recommended consumption quantity of the particular food item is at least partially based on the estimated caloric value.

7. The electronic device of claim 1, wherein the recommended consumption quantities are further based on a food consumption history of a user associated with the electronic device.

8. The electronic device of claim 1, further comprising:
a communication interface,
wherein the instructions are further executable by the at least one processor to cause the electronic device to:
receive information on a caloric consumption of a user of the electronic device through the communication interface, and
wherein the recommended consumption quantities is based on the received information on the caloric consumption.

9. The electronic device of claim 1, wherein the instructions are further executable by the at least one processor to cause the electronic device to:
obtain abstract information on at least one food item from among the plurality of food items and display the abstraction information superimposed over the image; and
in response to detecting an input, changing the display of the abstract information to detailed information for the at least one food item.

10. The electronic device of claim 9, further comprising:
a communication interface,
wherein the detailed information comprises at least one icon for accessing at least one web site, and
wherein the instructions are further executable by the at least one processor to cause the electronic device to access the at least one website using the communication interface in response to detecting selection of the at least one icon.

11. The electronic device of claim 1, wherein the instructions are further executable by the at least one processor to cause the electronic device to:
visually distinguishably display at least one among a texture, a color, or brightness of each of the plurality of food items based on nutrients of each of the plurality of food items.

12. An electronic device comprising:
at least one camera;
at least one display;
at least one processor; and
a memory storing instructions executable by the at least one processor to cause the electronic device to:
capture and display an image, using the at least one camera, including a plurality of food items;
identify the plurality of food items in the image, including a first food item and a second food item;
obtain nutritional information corresponding to each of the plurality of food items;
obtain recommendation information including recommended consumption quantities associated with each of the plurality of food items based on the nutritional information, including a first recommended consumption quantity for the first food item and a second recommended consumption quantity for the second food item;
display a plurality of indications superimposed on the displayed image to represent recommended consumption quantities for each of the plurality of food items included in the displayed image, the indications including at least a first indication superimposed on a first food item and a second indication superimposed on a second food item; and
in response to detecting a user input selecting the first displayed indication, altering a visual size of the first displayed indication to set a new target consumption quantity for the first food item, and altering a visual size of the second displayed indication to represent a change in the second recommended consumption quantity of the second food item according to the new target consumption quantity of the first food item, such that a total consumption quantity of the plurality of food items is maintained.

13. The electronic device of claim 12, wherein the displayed indications further include a third indication associated with a third food item, the instructions further executable by the at least one processor to cause the electronic device to:

terminate display of the third indication responsive to the user input.

14. The electronic device of claim 12, wherein at least one of the indications includes a highlighting effect imposed over a portion of one food item less than an entirety of the food item, the highlighting effect indicating a recommended consumption quantity of the food item.

15. The electronic device of claim 12, wherein the input to the first indication altering the size of the first food item includes a multi-touch drag input to the first food item as displayed within the image obtained using the at least one camera, and
   wherein when the visual size of the first indication is enlarged, the size of the second indication is reduced, to maintain the total consumption quantity of the plurality of food items.

16. The electronic device of claim 15, wherein the instructions are further executable by the at least one processor to cause the electronic device to:
   display a total caloric value of each of the food items, wherein the enlarged size of the first indication and the reduced size of the second indication are displayed simultaneously superimposed over the displayed image obtained using the at least one camera.

17. The electronic device of claim 16, wherein the total caloric value is calculated at least partially based on depth information which is used to estimate a scale and a weight of each of the food items.

18. The electronic device of claim 12, wherein the user input comprises a drag input to the first indication.

19. The electronic device of claim 12, wherein the recommended consumption quantity of each food item is obtained based on biometric information on a user associated with the electronic device.

20. The electronic device of claim 12, wherein the instructions are further executable by the at least one processor to cause the electronic device to:
   visually distinguishably display at least one among a texture, a color, or brightness of each of the plurality of food items based on nutrients of each of the plurality of food items.

* * * * *